US012209117B2

United States Patent
Bornholdt et al.

(10) Patent No.: US 12,209,117 B2
(45) Date of Patent: *Jan. 28, 2025

(54) MONOCLONAL ANTIBODIES AND COCKTAILS FOR TREATMENT OF EBOLA INFECTIONS

(71) Applicants: Mapp Biopharmaceutical, Inc., San Diego, CA (US); Albert Einstein College of Medicine, Bronx, NY (US); Adimab, LLC, Lebanon, NH (US)

(72) Inventors: Zachary A. Bornholdt, Encinitas, CA (US); Larry Zeitlin, San Diego, CA (US); Kartik Chandran, Brooklyn, NY (US); Anna Wec, Lebanon, NH (US); Laura Walker, Norwich, VT (US)

(73) Assignees: Biopharmaceutical, Inc., San Diego, CA (US); Albert Einstein College of Medicine, Bronx, NY (US); Adimab, LLC, Lebanon, NH (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/856,774

(22) Filed: Jul. 1, 2022

(65) Prior Publication Data

US 2023/0044044 A1 Feb. 9, 2023

Related U.S. Application Data

(63) Continuation of application No. 16/897,027, filed on Jun. 9, 2020, now Pat. No. 11,407,817, and a continuation of application No. 16/897,013, filed on Jun. 9, 2020, now Pat. No. 11,407,816, said application No. 16/897,027 is a continuation of application No. 15/898,524, filed on Feb. 17, 2018, now Pat. No. 10,836,810, said application No. 16/897,013 is a continuation of application No. 15/898,524, filed on Feb. 17, 2018, now Pat. No. 10,836,810.

(60) Provisional application No. 62/460,200, filed on Feb. 17, 2017.

(51) Int. Cl.
| | |
|---|---|
| *C07K 16/10* | (2006.01) |
| *A61K 39/42* | (2006.01) |
| *A61P 31/14* | (2006.01) |
| *A61K 39/00* | (2006.01) |

(52) U.S. Cl.
CPC .............. *C07K 16/10* (2013.01); *A61P 31/14* (2018.01); *A61K 39/42* (2013.01); *A61K 2039/505* (2013.01); *A61K 2039/545* (2013.01); *A61K 2039/55* (2013.01); *A61K 2039/57* (2013.01); *A61K 2039/6075* (2013.01); *A61K 2039/62* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,020,153 A | 2/2000 | Hardman et al. |
| 6,120,767 A | 9/2000 | Robinson et al. |
| 6,204,023 B1 | 3/2001 | Robinson et al. |
| 6,461,824 B1 | 10/2002 | Better et al. |
| 6,630,144 B1 | 10/2003 | Hart et al. |
| 6,875,433 B2 | 4/2005 | Hart et al. |
| 8,513,391 B2 | 8/2013 | Jones et al. |
| 9,145,454 B2 | 9/2015 | Jones et al. |
| 9,249,214 B2 | 2/2016 | Jones et al. |
| 11,242,378 B2 | 2/2022 | Bornholdt et al. |
| 11,242,379 B2 | 2/2022 | Bornholdt et al. |
| 11,254,732 B2 | 2/2022 | Bornholdt et al. |
| 11,407,816 B2 | 8/2022 | Bornholdt et al. |
| 11,407,817 B2 | 8/2022 | Bornholdt et al. |
| 2003/0235578 A1 | 12/2003 | Stinson et al. |
| 2004/0053865 A1 | 3/2004 | Hart et al. |
| 2006/0024292 A1 | 2/2006 | Gerngross et al. |
| 2009/0175886 A1 | 7/2009 | Black et al. |
| 2011/0217305 A1 | 9/2011 | Pedersen et al. |
| 2012/0082667 A1 | 4/2012 | Yokoseki et al. |
| 2012/0195909 A1 | 8/2012 | Medema et al. |
| 2013/0096282 A1 | 4/2013 | Neville |
| 2013/0149300 A1 | 6/2013 | Hiatt et al. |
| 2015/0232538 A1 | 8/2015 | Jones et al. |
| 2016/0324965 A1 | 11/2016 | Hiatt et al. |

(Continued)

FOREIGN PATENT DOCUMENTS

| | | |
|---|---|---|
| WO | 2004018649 | 3/2004 |
| WO | 2004050032 | 6/2004 |
| WO | 2005034733 | 4/2005 |

(Continued)

OTHER PUBLICATIONS

"*Homo Sapiens* Isolate ADI-15946-VH Immunoglobulin Heavy Chain V Region mRNA, Partial cds", GenBank Accession No. KU602499, , Available Online at: https://www.ncbi.nlm.nih.gov/nuccore/KU602499.1, Feb. 27, 2016, 1 page.

(Continued)

*Primary Examiner* — Stacy B Chen
(74) *Attorney, Agent, or Firm* — Kilpatrick Townsend & Stockton LLP

(57) ABSTRACT

Described herein are compositions and methods for the prevention and treatment of ebolavirus infection. In certain embodiments of the present invention, monoclonal antibodies substantially similar to those described herein, as well as affinity matured variants thereof, alone or in combination, provide therapeutic efficacy in a patient against multiple species of ebolavirus.

18 Claims, 13 Drawing Sheets

Specification includes a Sequence Listing.

(56) References Cited

U.S. PATENT DOCUMENTS

2016/0326234 A1 11/2016 Hiatt et al.

FOREIGN PATENT DOCUMENTS

| WO | 2005094879 | 10/2005 |
|---|---|---|
| WO | 2009055054 | 4/2009 |
| WO | 2010045388 | 4/2010 |
| WO | 2011085103 | 7/2011 |
| WO | 2015127136 | 8/2015 |
| WO | 2016033570 | 3/2016 |
| WO | 2016054598 | 4/2016 |
| WO | 2017156423 | 9/2017 |

OTHER PUBLICATIONS

"Homo Sapiens Isolate ADI-15946-VK Immunoglobulin Heavy Chain V Region mRNA, Partial cds", GenBank Accession No. KU602500, Feb. 27, 2016, 1 page.

U.S. Appl. No. 16/897,013, Non-Final Office Action, Mailed On Oct. 28, 2021, 12 pages.

U.S. Appl. No. 16/897,013, Notice of Allowance, Mailed On Apr. 5, 2022, 14 pages.

U.S. Appl. No. 16/897,027, Non-Final Office Action, Mailed On Oct. 28, 2021, 12 pages.

U.S. Appl. No. 16/897,027, Notice of Allowance, Mailed On Apr. 5, 2022, 14 pages.

Almagro et al., "Humanization of Antibodies", Frontiers in Bioscience, vol. 13, No. 5, Jan. 1, 2008, pp. 1619-1633.

Audet et al., "Molecular Characterization of the Monoclonal Antibodies Composing ZMAb: A Protective Cocktail Against Ebola Virus", Scientific Reports, vol. 4, No. 6881, 2014, 8 pages.

Bornholdt et al., "Host-Primed Ebola Virus GP Exposes a Hydrophobic NPC1 Receptor-Binding Pocket, Revealing a Target for Broadly Neutralizing Antibodies", American Society for Microbiology Journals, vol. 7, No. 1, Jan.-Feb. 2016, 11 pages.

Bornholdt et al., "Isolation of Potent Neutralizing Antibodies from a Survivor of the 2014 Ebola Virus Outbreak", Science, vol. 351, No. 6277, Available Online at: https://science.sciencemag.org/content/sci/su ppl/2016/02/17 /science .aad5788. DC 1 /aad5788-BornholdtSM.pdf, Mar. 4, 2016, pp. 1078-1083.

Bornholdt et al., "Supplementary Materials for Isolation of Potent Neutralizing Antibodies from a Survivor of the 2014 Ebola Virus Outbreak", Materials and Methods, Figs. S1 to S14, Tables S1 to S7, References (31-39), Feb. 18, 2016, 39 pages.

Castilho et al., "In Planta Protein Sialylation through Overexpression of the Respective Mammalian Pathway", The Journal of Biological Chemistry, vol. 285, No. 21, May 21, 2010, pp. 15923-15930.

Chen et al., "Generation and Analysis of Random Point Mutations in An Antibody CDR2 Sequence: Many Mutated Antibodies Lose Their Ability to Bind Antigen", Journal of Experimental Medicine, vol. 176, Sep. 1, 1992, pp. 855-866.

Druar et al., "Analysis of the Expressed Heavy Chain Variable-region Genes of Macaca Fascicularis and Isolation of Monoclonal Antibodies Specific for the Ebola Virus' Soluble Glycoprotein", Immunogenetics, vol. 57, No. 10, Nov. 2005, pp. 730-738.

Application No. EP18754083.6, Extended European Search Report, Mailed On Oct. 14, 2020, 9 pages.

Jahrling et al., "Ebola Hemorrhagic Fever: Evaluation of Passive Immunotherapy in Nonhuman Primates", The Journal of Infectious Diseases, vol. 196, Suppl 2, Nov. 15, 2007, pp. S400-S403.

Jones, "Therapeutic Antibodies to Ebola and Marburg Viruses", Proceedings of the CRTI 2006 Summer Symposium, CRTI 0087RD, XP009143369, Jun. 13, 2006.

Application No. JP2019-544840, Office Action, Mailed On Jan. 7, 2022, 12 pages.

Kashimiri et al., "SDR Grafting—a New Approach to Antibody Humanization", Methods, vol. 36, No. 1, May 2005, pp. 25-34.

Li et al., "The I Binding Specificity of Human VH 4-34 (VH 4-21) Encoded Antibodies is Determined by both VH Framework Region 1 and Complementarity Determining Region 3", Journal of Molecular Biology, vol. 256, No. 3, Mar. 1, 1996.

Olimpier et al., "Prediction of Site-specific Interactions in Antibody-antigen Complexes: the ProABC Method and Server", Bioinformatics, vol. 29, No. 18, Sep. 15, 2013, pp. 2285-2291.

Olimpier et al., "Supplemental Material: Prediction of Site-Specific Interactions in Antibody-Antigen Complexes: The ProABC Method and Server", Bioinformatics, vol. 29, No. 18, Sep. 15, 2013, 10 pages.

Olinger Jr. et al., "Delayed Treatment of Ebola Virus Infection With Plant-derived Monoclonal Antibodies Provides Protection in Rhesus Macaques", Proceedings of the National Academy of Sciences of the United States of America, vol. 109, No. 44, Oct. 30, 2012, pp. 18030-18035.

Oswald et al., "Neutralizing Antibody Fails to Impact the Course of Ebola Virus Infection in Monkeys", PLOS Pathogens, vol. 3, No. 1, Jan. 2007, 5 pages.

Parren et al., "Pre- and Postexposure Prophylaxis of Ebola Virus Infection in an Animal Model by Passive Transfer of a Neutralizing Human Antibody", Journal of Virology, vol. 76, No. 12, Jun. 2002, pp. 6408-6412.

Paul, "Fv Structure and Diversity in Three Dimensions", Fundamental Immunology Third Edition, 1993, pp. 292-295.

Pettitt et al., "Therapeutic Intervention of Ebola Virus Infection in Rhesus Macaques With the Mb-003 Monoclonal Antibody Cocktail", Science Translational Medicine, vol. 5, No. 199, Aug. 21, 2013.

Qiu et al., "Reversion of Advanced Ebola Virus Disease in Nonhuman Primates with Zmapp", Nature, vol. 514, Issue 7520, Oct. 2, 2014, 15 pages.

Qiu et al., "Successful Treatment of Ebola Virus-infected Cynomolgus Macaques with Monoclonal Antibodies", Science Translational Medicine, vol. 4, No. 138, Jun. 13, 2012.

Qiu et al., "Sustained Protection Against Ebola Virus Infection Following Treatment of Infected Nonhuman Primates With ZMAb", Scientific Reports vol. 3,No. 3365, Nov. 28, 2013, pp. 1-9.

Qui et al., "mAbs and Ad-Vectored IFN-α Therapy Rescue Ebola-Infected Nonhuman Primates when Administered after the Detection of Viremia and Symptoms", Science Translation Medicine, vol. 5, No. 207, Oct. 16, 2013.

Rudikoff et al., "Single Amino Acid Substitution Altering Antigen-Binding Specificity", Proceedings of the National Academy of Sciences of the USA; vol. 79, Issue 6, Mar. 1982, pp. 1979-1983.

Shahhosseini et al., "Production and Characterization of Monoclonal Antibodies Against Different Epitopes of Ebola Virus Antigensn", Journal of Virological Methods, vol. 143, No. 1, Jul. 2007, pp. 29-37.

Soltes et al., "On the Influence of Vector Design on Antibody Phage Display", Journal of Biotechnology, vol. 127, No. 4, Jan. 20, 2007, pp. 626-637.

Takada et al., "Protective Efficacy of Neutralizing Antibodies Against Ebola Virus Infectio", Vaccine, vol. 25, No. 6, Jan. 22, 2007, pp. 993-999.

Towner et al., "Newly Discovered Ebola Virus Associated with Hemorrhagic Fever Outbreak in Uganda", PLOS Pathogens, vol. 4, No. 11, Nov. 21, 2008, 6 pages.

Wec et al., "A "Trojan Horse" Bispecific-antibody Strategy for Broad Protection Against Ebolaviruses", Science, vol. 354, No. 6310, Oct. 21, 2016, pp. 350-354.

Wec et al., "Antibodies from a Human Survivor Define Sites of Vulnerability for Broad Protection against Ebolaviruses", Cell, vol. 169, No. 5, May 18, 2017, pp. 878-890.

Wec et al., "Development of a Human Antibody Cocktail that Deploys Multiple Functions to Confer Pan-Ebolavirus Protection", Cell Host & Microbe, vol. 25, No. 1, Jan. 9, 2019, pp. 39-48.

Winkler et al., "Changing The Antigen Binding Specificity By Single Point Mutations of An Anti-P24 (HIV-1) Antibody", The Journal of Immunology, vol. 165, No. 8, Oct. 15, 2000, pp. 4505-4514.

(56) References Cited

OTHER PUBLICATIONS

Xiang et al., "Framework Residues 71 and 93 of The Chimeric B72.3 Antibody are Major Determinants of The Conformation of Heavy-Chain Hypervariable Loops", J. Mol. Bioi., vol. 253, Oct. 27, 1995, pp. 385-390.

Xiang et al., "Light-Chain Framework Region Residue Tyr71 of Chimeric B72.3 Antibody Plays an Important Role in Influencing the TAG72 Antigen Binding", Protein Engineering, vol. 12, No. 5, May 1999, pp. 417-421.

Zeitlin et al., "Enhanced Potency of a Fucose-free Monoclonal Antibody Being Developed as an Ebola Virus Immunoprotectant", Proceedings of the National Academy of Sciences of the United States of America, vol. 108, No. 51, Dec. 20, 2011, pp. 20690-20694.

Application No. CA3,053,305, Office Action, Mailed On Jun. 28, 2023, 4 pages.

Application No. JP2022-130855, Office Action, Mailed On Aug. 1, 2023, 6 pages.

MBP134 vs EBOV/Kikwit in NHPs

- PBS Control (n=2)
- 25 mg/kg 4dpi
- 50 mg/kg 4dpi + 25 mg/kg 7dpi

Percent survival vs Days post-infection

Figure 11

A Single Dose of MBP134 Provides Complete Protection from SUDV Challenge in NHPs

Figure 12

MBP134 Provides Protection from BDBV/But-811250 Challenge in Cynos

Percent survival vs. Days post-infection

- Vehicle Control (n=3)
- 25 mg/kg 7dpi (n=6)

*All the animals had fevers and were PCR positive upon treatment*

Figure 13 rVSV Neutralization Curves for PE-293 vs PE-Plant vs PE-CHO derived mAbs

MONOCLONAL ANTIBODIES AND COCKTAILS FOR TREATMENT OF EBOLA INFECTIONS

CROSS-REFERENCE TO RELATED APPLICATIONS

This application is a continuation of U.S. patent application Ser. No. 16/897,013, filed Jun. 9, 2020, now U.S. Pat. No. 11,407,816, issued Aug. 9, 2022, which is a continuation of U.S. patent application Ser. No. 15/898,524, filed Feb. 17, 2018, now U.S. Pat. No. 10,836,810, issued Nov. 17, 2020, which claims the benefit of U.S. Provisional Patent Application No. 62/460,200, filed Feb. 17, 2017.

This application is a continuation of U.S. patent application Ser. No. 16/897,027, filed Jun. 9, 2020, now U.S. Pat. No. 11,407,817, issued Aug. 9, 2022, which is a continuation of U.S. patent application Ser. No. 15/898,524, filed Feb. 17, 2018, now U.S. Pat. No. 10,836,810, issued Nov. 17, 2020, which claims the benefit of U.S. Provisional Patent Application No. 62/460,200, filed Feb. 17, 2017, each of which is incorporated by reference herein in their entirety.

STATEMENT REGARDING FEDERALLY FUNDED RESEARCH

This invention was made with government support under U19 AI109762 awarded by NIH and HDTRA-13-C-0018 awarded by DTRA. The government has certain rights in the invention.

SEQUENCE LISTING

The instant application contains a Sequence Listing which has been submitted electronically in XML format and is hereby incorporated by reference in its entirety. Said XML copy, created on Aug. 10, 2022, is named 107942-1335552-000260US-SL.xml and is 72,604 bytes in size.

BACKGROUND

Ebolaviruses are members of the family Filoviridae which infect humans and non-human primates (NHPs) causing hemorrhagic fever with mortality rates up to 90%. Ebolaviruses include Ebola virus (EBOV), Sudan virus (SUDV), Bundibugyo virus (BDBV), Reston virus (RESTV), and Tai Forest virus (TAFV), which are causative agents of the hemorrhagic fever [1, 2]. A summary of the ebolaviruses can be found in Burk, et. al., Neglected Filoviruses. FEMS Microbiology Reviews, 40, 494-519 (May, 2016), and the differences between the viruses have been well characterized and well known in the art. Between 1967 and 2013, 31 filovirus disease outbreaks have occurred, mainly in central Africa with around 2,000 confirmed cases. Of these 31 outbreaks, 16 were caused by EBOV. The unprecedented 2013-2016 Ebola virus disease epidemic led to more than 27,000 cases and 11,100 deaths in the first 14 months. There are currently no approved treatments or vaccines for filoviruses, and most advanced experimental treatments focus only on EBOV. Given that other filoviruses have caused sizeable outbreaks broadly protective treatment options are urgently needed.

Several studies have shown that filovirus glycoprotein (GP)-specific neutralizing antibodies (nAbs) can reduce mortality following experimental inoculation of animals with a lethal dose of EBOV [3-9]. The primary target of these neutralizing antibodies, the filovirus surface GP, is a trimer composed of three heavily glycosylated GP1-GP2 heterodimers. The GP1 subunit can be divided further into base, head, glycan cap and mucin-like domains [10]. During viral entry, the mucin-like domain and glycan cap mediate binding to multiple host attachment factors present on the cell membrane. After the virus enters the host cell by macropinocytosis [11, 12] the GP is cleaved by host proteases that remove approximately 80% of the mass of the GP1 subunit, including the mucin-like domain and glycan cap [13, 14]. After cleavage of GP in the endosome, the receptor binding sites on GP become exposed, and the GP1 head then is able to bind its receptor, the Niemann-Pick C1 (NPC1) protein [13, 15, 16]. Subsequent conformational changes in GP facilitate fusion between viral and endosomal membranes. Recognition of NPC1 by a cleaved GP species (hereafter, $GP_{CL}$), together with one or more unknown host signals, is proposed to trigger GP refolding and the membrane fusion reaction that is coupled to it. Endosomal $GP \rightarrow GP_{CL}$ cleavage is a prerequisite for GP-NPC1 binding and therefore essential for filovirus entry.

The dense clustering of glycans on the glycan cap and mucin-like domain likely shield much of the surface of EBOV GP from humoral immune surveillance, leaving only a few sites on the EBOV GP protein where nAbs could bind without interference by glycans [17]. Most of our knowledge about humoral response against filovirus infections has come from studies of murine Abs that recognize EBOV GP. From those studies, it has become clear that mouse neutralizing Abs preferentially target peptides exposed in upper, heavily glycosylated domains or lower areas (the GP1 base) where rearrangements occur that drive fusion of viral and host membranes [18]. Abs have not been identified that target protein features of the membrane proximal external region (MPER) subdomain, which likely rearranges during fusion. KZ52, the first reported human EBOV GP-specific monoclonal antibody (mAb), was obtained from a phage display library that was constructed from bone marrow RNA obtained from a survivor [19]. KZ52 binds a site at the base of the GP and neutralizes EBOV, most likely by blocking $GP \rightarrow GP_{CL}$ cleavage and/or inhibiting the conformational changes required for fusion of viral and endosomal membranes [10]. Some murine Abs also have been reported to bind to the base region of Ebola virus GPs [20, 21].

The most divergent ebolavirus species (EBOV and SUDV) exhibit 56% GP sequence identity. The sequence identity between filovirus GPs is highest within the receptor binding region (RBR) [23] and GP2, suggesting that shared epitopes may exist within these domains. Several mAbs against EBOV GP with protective efficacy in rodents and non-human primates (NHPs) have been reported [3, 5-9, 24, 25]. Neutralizing antibodies have also been described for SUDV with efficacy in a recently developed rodent model [20, 26]. However, these antibodies bind the same epitope as KZ52, and like KZ52 are viral species-specific and lack cross-neutralizing or cross-protective properties.

SUMMARY OF THE INVENTION

Described herein are a number of mAbs that are capable of neutralizing Ebola viruses both in vitro and in vivo. Surprisingly, the disclosed human antibodies possess pan-ebolavirus cross-reactivity and cross-neutralizing activity, and are thus capable of binding and neutralizing all known species of the Ebola virus.

According to a first aspect of the present invention, there are provided novel monoclonal antibodies capable of binding to and neutralizing an Ebola virus in a patient. In certain embodiments of the present invention, said monoclonal antibodies bind to GP proteins from ebolaviruses belonging to at least two different species, thereby neutralizing the infectivity of viral particles or targeting infected cells for destruction.

According to a second aspect of the invention, there is provided monoclonal antibodies comprising the following heavy and light chain CDR3 amino acid sequences:

mAb PE-87-heavy CDR3: SEQ ID No. 1; mAb PE-87-light CDR3: SEQ ID No. 2
mAb PE-24-heavy CDR3: SEQ ID No. 3; mAb PE-24-light CDR3: SEQ ID No. 4
mAb PE-47-heavy CDR3: SEQ ID No. 5; mAb PE-47 light CDR3: SEQ ID No. 6
mAb PE-16-heavy CDR3: SEQ ID No. 7; mAb PE-16-light CDR3: SEQ ID No. 8
mAb PE-05-heavy CDR3: SEQ ID No. 9; mAb PE-05-light CDR3: SEQ ID No. 10

In one embodiment, the critical residues in PE-87 and PE-24 heavy chain CDR3 are D95, W99, and Y100C (Kabat numbering).

In another embodiment of the invention, an antibody isolated as described in Methods (below) from the peripheral B cells of a survivor of a Filovirus infection, is modified so that the VH and VL region nucleotide sequences encode modified V region amino acids that confer enhanced binding capabilities to the mAb. There is provided a method of preparing a recombinant antibody comprising: providing a nucleotide sequence selected from the group consisting of
PE-24, PE-87, PE-47, PE-16, PE-64 and PE-05 VH and VL nucleotides;
modifying said nucleic acid sequence such that at least one but fewer than about 30 of the amino acid residues encoded by said nucleic acid sequence has been changed or deleted without disrupting antigen binding of said peptide; and expressing and recovering said modified nucleotide sequence.

In yet other embodiments, immunoreactive fragments of any of the herein described monoclonal antibodies are prepared using means known in the art, for example, by preparing nested deletions using enzymatic degradation or convenient restriction enzymes.

It is another aspect of the present invention to provide modified variants of the disclosed mAb sequences, wherein the sequences have been affinity matured or otherwise mutated to increase the therapeutic effectiveness of the mAb.

Thus, it is one embodiment of the present invention to provide a composition for the treatment of Ebola, the composition comprising: a therapeutically effective combination of a first monoclonal antibody or antigen binding fragment comprising a heavy chain variable region comprising an amino acid sequence at least 90% identical to SEQ. ID NO: 12, and affinity matured variants thereof; and a light chain variable region comprising an amino acid sequence at least 90% identical to SEQ ID NO: 14, and affinity matured variants thereof; and a pharmaceutically acceptable excipient or carrier.

It is another embodiment of the present invention to provide such a composition, wherein said first monoclonal antibody is binds at least two species of the Flivovirus glycoprotein.

It is yet another embodiment of the present invention to provide such a composition, wherein the first monoclonal antibody or antigen binding fragment comprises predominantly a single glycoform.

It is still another embodiment of the present invention to provide such a composition, wherein the predominantly single glycoform is one of GnGn, G1/G2, and NaNa.

It is yet another embodiment of the present invention to provide such a composition, wherein the predominantly single glycoform substantially lacks at least one of fucose and xylose.

It is second embodiment of the present invention to provide a composition for the treatment of Ebola, the composition comprising: a therapeutically effective combination of a first monoclonal antibody or antigen binding fragment selected from a list consisting of:

a. a monoclonal antibody or antigen binding fragment comprising a heavy chain variable region comprising an amino acid sequence at least 90% identical to SEQ. ID NO: 15, and affinity matured variants thereof; and a light chain variable region comprising an amino acid sequence at least 90% identical to SEQ ID NO: 18, and affinity matured variants thereof;

b. a monoclonal antibody or antigen binding fragment comprising a heavy chain variable region comprising an amino acid sequence at least 90% identical to SEQ. ID NO: 21, and affinity matured variants thereof; and a light chain variable region comprising an amino acid sequence at least 90% identical to SEQ ID NO: 23, and affinity matured variants thereof;

c. a monoclonal antibody or antigen binding fragment comprising a heavy chain variable region comprising an amino acid sequence at least 90% identical to SEQ. ID NO: 29, and affinity matured variants thereof; and a light chain variable region comprising an amino acid sequence at least 90% identical to SEQ ID NO: 31, and affinity matured variants thereof;

d. a monoclonal antibody or antigen binding fragment comprising a heavy chain variable region comprising an amino acid sequence at least 90% identical to SEQ. ID NO: 33, and affinity matured variants thereof; and a light chain variable region comprising an amino acid sequence at least 90% identical to SEQ ID NO: 35, and affinity matured variants thereof;

e. a monoclonal antibody or antigen binding fragment comprising a heavy chain variable region comprising an amino acid sequence at least 90% identical to SEQ. ID NO: 11, and affinity matured variants thereof; and a light chain variable region comprising an amino acid sequence at least 90% identical to SEQ ID NO: 13, and affinity matured variants thereof; and a pharmaceutically acceptable excipient or carrier; wherein said first monoclonal antibody or antigen binding fragment binds at least two species of the Flivovirus glycoprotein.

It is another embodiment of the present invention to provide such a composition, wherein the first monoclonal antibody or antigen binding fragment comprises predominantly a single glycoform.

It is yet another embodiment of the present invention to provide such a composition, wherein the predominantly single glycoform is one of GnGn, C1/G2, and NaNa.

It is still another embodiment of the present invention to provide such a composition, wherein the predominantly single glycoform substantially lacks at least one of fucose and xylose.

It is third embodiment of the present invention to provide a composition for the treatment of Ebola, the composition comprising: a therapeutically effective combination of a first monoclonal antibody or antigen binding fragment is selected from a list consisting of:

a. a monoclonal antibody or antigen binding fragment comprising a heavy chain variable region comprising an amino acid sequence at least 90% identical to SEQ. ID NO: 12, and affinity matured variants thereof; and a light chain variable region comprising an amino acid sequence at least 90% identical to SEQ ID NO: 14, and affinity matured variants thereof;

b. a monoclonal antibody or antigen binding fragment comprising a heavy chain variable region comprising an amino acid sequence at least 90% identical to SEQ. ID NO: 15, and affinity matured variants thereof; and a light chain variable region comprising an amino acid sequence at least 90% identical to SEQ ID NO: 18, and affinity matured variants thereof;

c. a monoclonal antibody or antigen binding fragment comprising a heavy chain variable region comprising an amino acid sequence at least 90% identical to SEQ. ID NO: 21, and affinity matured variants thereof; and a light chain variable region comprising an amino acid sequence at least 90% identical to SEQ ID NO: 23, and affinity matured variants thereof;

d. a monoclonal antibody or antigen binding fragment comprising a heavy chain variable region comprising an amino acid sequence at least 90% identical to SEQ. ID NO: 29, and affinity matured variants thereof; and a light chain variable region comprising an amino acid sequence at least 90% identical to SEQ ID NO: 31, and affinity matured variants thereof;

e. a monoclonal antibody or antigen binding fragment comprising a heavy chain variable region comprising an amino acid sequence at least 90% identical to SEQ. ID NO: 33, and affinity matured variants thereof; and a light chain variable region comprising an amino acid sequence at least 90% identical to SEQ ID NO: 35, and affinity matured variants thereof;

f. a monoclonal antibody or antigen binding fragment comprising a heavy chain variable region comprising an amino acid sequence at least 90% identical to SEQ. ID NO: 11, and affinity matured variants thereof; and a light chain variable region comprising an amino acid sequence at least 90% identical to SEQ ID NO: 13, and affinity matured variants thereof; a second monoclonal antibody or antigen binding fragment, wherein said second monoclonal antibody or antigen binding fragment binds the Ebola glycoprotein; and a pharmaceutically acceptable excipient or carrier.

It is another embodiment of the present invention to provide such a composition, wherein at least one of the first monoclonal antibody or antigen binding fragment and the second antibody or antigen binding fragment comprises predominantly a single glycoform.

It is yet another embodiment of the present invention to provide such a composition, wherein the predominantly single glycoform is one of GnGn, G1/G2, and NaNa.

It is still another embodiment of the present invention to provide such a composition, wherein the predominantly single glycoform substantially lacks at least one of fucose and xylose.

It is yet another embodiment of the present invention to provide such a composition, wherein said therapeutically effective combination further comprises a third monoclonal antibody or antigen binding fragment that binds to the Ebola glycoprotein.

It is still another embodiment of the present invention to provide such a composition, wherein said first monoclonal antibody or antigen binding fragment comprises a heavy chain variable region comprising an amino acid sequence at least 90% identical to SEQ. ID NO: 12, and affinity matured variants thereof; and a light chain variable region comprising an amino acid sequence at least 90% identical to SEQ ID NO: 14, and affinity matured variants thereof; and wherein said second monoclonal antibody or antigen binding fragment comprises a heavy chain variable region comprising an amino acid sequence at least 90% identical to SEQ. ID NO: 15, and affinity matured variants thereof; and a light chain variable region comprising an amino acid sequence at least 90% identical to SEQ ID NO: 18, and affinity matured variants thereof.

It is yet another embodiment of the present invention to provide such a composition wherein said therapeutically effective combination further comprises a third monoclonal antibody or antigen binding fragment, wherein said third antibody or antigen binding fragment comprises a heavy chain variable region comprising an amino acid sequence at least 90% identical to SEQ. ID NO: 21, and affinity matured variants thereof; and a light chain variable region comprising an amino acid sequence at least 90% identical to SEQ ID NO: 23, and affinity matured variants thereof.

It is fourth embodiment of the present invention to provide a method for treating at least one species of flivovirus infection in a patient, the method comprising: identifying a patient in need of treatment; and administering to the patient a therapeutically effective amount of a composition comprising a combination of: a first monoclonal antibody or antigen binding fragment, wherein said first monoclonal antibody or antigen binding fragment is selected from a list consisting of:

i. a monoclonal antibody or antigen binding fragment comprising a heavy chain variable region comprising an amino acid sequence at least 90% identical to SEQ. ID NO: 12, and affinity matured variants thereof; and a light chain variable region comprising an amino acid sequence at least 90% identical to SEQ ID NO: 14, and affinity matured variants thereof;

ii. a monoclonal antibody or antigen binding fragment comprising a heavy chain variable region comprising an amino acid sequence at least 90% identical to SEQ. ID NO: 15, and affinity matured variants thereof; and a light chain variable region comprising an amino acid sequence at least 90% identical to SEQ ID NO: 18, and affinity matured variants thereof;

iii. a monoclonal antibody or antigen binding fragment comprising a heavy chain variable region comprising an amino acid sequence at least 90% identical to SEQ. ID NO: 21, and affinity matured variants thereof; and a light chain variable region comprising an amino acid sequence at least 90% identical to SEQ ID NO: 23, and affinity matured variants thereof;

iv. a monoclonal antibody or antigen binding fragment comprising a heavy chain dvariable region comprising an amino acid sequence at least 90% identical to SEQ. ID NO: 29, and affinity matured variants thereof; and a light chain variable region comprising an amino acid sequence at least 90% identical to SEQ ID NO: 31, and affinity matured variants thereof;

v. a monoclonal antibody or antigen binding fragment comprising a heavy chain variable region comprising an amino acid sequence at least 90% identical to SEQ. ID NO: 33, and affinity matured variants thereof; and a light chain variable region comprising an amino acid sequence at least 90% identical to SEQ ID NO: 35, and affinity matured variants thereof;

vi. a monoclonal antibody or antigen binding fragment comprising a heavy chain variable region comprising an amino acid sequence at least 90% identical to SEQ. ID NO: 11, and affinity matured variants thereof; and a light chain variable region comprising an amino acid sequence at least 90% identical to SEQ ID NO: 13, and affinity matured variants thereof; and a pharmaceutically acceptable excipient or carrier.

It is another embodiment of the present invention to provide such a method, wherein the patient is a mammal.

It is yet another embodiment of the present invention to provide such a method, wherein the first monoclonal antibody or antigen binding fragment comprises predominantly a single glycoform.

It is still another embodiment of the present invention to provide such a method, wherein the predominantly single glycoform substantially lacks at least one of fucose and xylose.

It is fifth embodiment of the present invention to provide a composition for the treatment of Ebola, the composition comprising: a therapeutically effective combination of a first monoclonal antibody or antigen binding fragment is selected from a list consisting of:
- a. a monoclonal antibody or antigen binding fragment comprising a heavy chain variable region at least 90% identical to a heavy chain variable region comprising a CDR1 comprising the amino acid sequence as set forth in SEQ. ID NO: 53, a CDR2 comprising the amino acid sequence as set forth in SEQ. ID NO: 54, and a CDR3 comprising the amino acid sequence as set forth in SEQ. ID NO: 55, and affinity matured variants thereof; and a light chain variable region at least 90% identical to a light chain variable region comprising a CDR1 comprising the amino acid sequence as set forth in SEQ. ID NO: 56, a CDR2 comprising the amino acid sequence as set forth in SEQ. ID NO: 57, and a CDR3 comprising the amino acid sequence as set forth in SEQ. ID NO: 58, and affinity matured variants thereof;
- b. a monoclonal antibody or antigen binding fragment comprising a heavy chain variable region at least 90% identical to a heavy chain variable region comprising a CDR1 comprising the amino acid sequence as set forth in SEQ. ID NO: 41, a CDR2 comprising the amino acid sequence as set forth in SEQ. ID NO: 42, and a. CDR3 comprising the amino acid sequence as set forth in SEQ. ID NO: 43, and affinity matured variants thereof; and a light chain variable region at least 90% identical to a light chain variable region comprising a CDR1 comprising the amino acid sequence as set forth in SEQ. ID NO: 44, a CDR2 comprising the amino acid sequence as set forth in SEQ. ID NO: 45, and a CDR3 comprising the amino acid sequence as set forth in SEQ. ID NO: 46, and affinity matured variants thereof;
- c. a monoclonal antibody or antigen binding fragment comprising a heavy chain variable region at least 90% identical to a heavy chain variable region comprising a CDR1 comprising the amino acid sequence as set forth in SEQ. ID NO: 47, a CDR2 comprising the amino acid sequence as set forth in SEQ. ID NO: 48, and a CDR3 comprising the amino acid sequence as set forth in SEQ. ID NO: 49, and affinity matured variants thereof; and a light chain variable region at least 90% identical to a light chain variable region comprising a CDR1 comprising the amino acid sequence as set forth in SEQ. ID NO: 50, a CDR2 comprising the amino acid sequence as set forth in SEQ. ID NO: 51, and a CDR3 comprising the amino acid sequence as set forth in SEQ. ID NO: 52, and affinity matured variants thereof;
- d. a monoclonal antibody or antigen binding fragment comprising a heavy chain variable region at least 90% identical to a heavy chain variable region comprising a CDR1 comprising the amino acid sequence as set forth in SEQ. ID NO: 59, a CDR2 comprising the amino acid sequence as set forth in SEQ. ID NO: 60, and a CDR3 comprising the amino acid sequence as set forth in SEQ. ID NO: 61, and affinity matured variants thereof; and a light chain variable region at least 90% identical to a light chain variable region comprising a CDR1 comprising the amino acid sequence as set forth in SEQ. ID NO: 62, a CDR2 comprising the amino acid sequence as set forth in SEQ. ID NO: 63, and a CDR3 comprising the amino acid sequence as set forth in SEQ. ID NO: 64, and affinity matured variants thereof;
- e. a monoclonal antibody or antigen binding fragment comprising a heavy chain variable region at least 90% identical to a heavy chain variable region comprising a CDR1 comprising the amino acid sequence as set forth in SEQ. ID NO: 65, a CDR2 comprising the amino acid sequence as set forth in SEQ. ID NO: 66, and a CDR3 comprising the amino acid sequence as set forth in SEQ. ID NO: 67, and affinity matured variants thereof; and a light chain variable region at least 90% identical to a light chain variable region comprising a CDR1 comprising the amino acid sequence as set forth in SEQ. ID NO: 68, a CDR2 comprising the amino acid sequence as set forth in SEQ. ID NO: 69, and a CDR3 comprising the amino acid sequence as set forth in SEQ. ID NO: 70, and affinity matured variants thereof;
- f. a monoclonal antibody or antigen binding fragment comprising a heavy chain variable region at least 90% identical to a heavy chain variable region comprising a CDR1 comprising the amino acid sequence as set forth in SEQ. ID NO: 71, a CDR2 comprising the amino acid sequence as set forth in SEQ. ID NO: 72, and a CDR3 comprising the amino acid sequence as set forth in SEQ. ID NO: 73, and affinity matured variants thereof; and a light chain variable region at least 90% identical to a light chain variable region comprising a CDR1 comprising the amino acid sequence as set forth in SEQ. ID NO: 74, a CDR2 comprising the amino acid sequence as set forth in SEQ. ID NO: 75, and a CDR3 comprising the amino acid sequence as set forth in SEQ. ID NO: 76, and affinity matured variants thereof; and a pharmaceutically acceptable excipient or carrier.

It is another embodiment of the present invention to provide such a composition, further comprising a second monoclonal antibody or antigen binding fragment, wherein said second monoclonal antibody or antigen binding fragment binds the Ebola glycoprotein.

It is yet another embodiment of the present invention to provide such a composition, wherein said first monoclonal antibody is binds at least two species of the Flivovirus glycoprotein.

It is still another embodiment of the present invention to provide such a composition, wherein the first monoclonal antibody or antigen binding fragment comprises predominantly a single glycoform.

It is yet another embodiment of the present invention to provide such a composition, wherein the predominantly single glycoform is one of GnGn, G1/G2, and NaNa.

It is still another embodiment of the present invention to provide such a composition, wherein the predominantly single glycoform substantially lacks at least one of fucose and xylose.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

DESCRIPTION OF THE FIGURES AND TABLES

Table 1. Amino acid residues comprising CDRs of anti-Ebola mAbs.

FIG. 3 shows the location of the mutations that result in escape mutant resistance to two monoclonal antibodies of the present invention.

Figure 9:
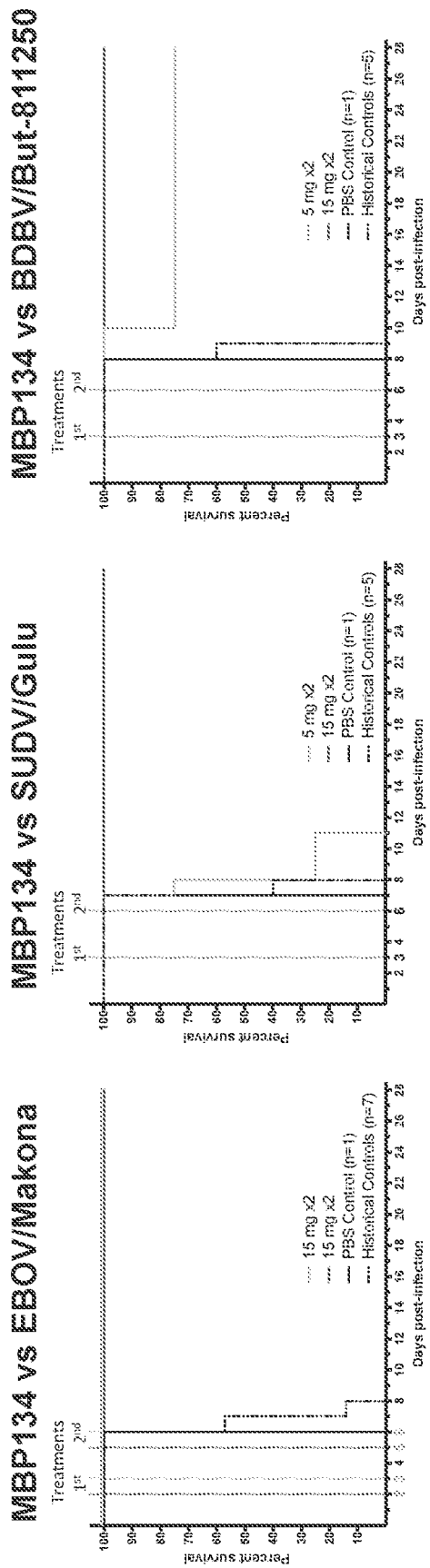

FIG. 9 survival data for ebolavirus infected guinea pigs treated with certain embodiments of the present invention.

FIG. 10 survival data for ebolavirus infected non-human primates treated with certain embodiments of the present invention.

FIG. 11 survival data for ebolavirus infected non-human primates treated with certain embodiments of the present invention.

FIG. 12 survival data for ebolavirus infected non-human primates treated with certain embodiments of the present invention.

FIG. 13 shows a neutralization curves for certain embodiments of the present invention created using differing production methods.

Table 2 shows the efficiency of anti-GP antibody isolation from peripheral B cells.

Table 3 shows the cross-reactivity of candidate pan-ebolavirus mAbs against different ebolavirus species. Reactivity was measured by ELISA.

Table 4 shows the in vitro neutralization activity and affinities of candidate pan-ebolavirus mAbs.

Table 5 shows that mice infected with EBOV and subsequently treated with the monoclonal antibodies described above showed increased survival compared to mice treated with PBS.

Table 6 is a summary of rVSV-GP neutralization by cross-neutralizing human mAb s.

Table 7 is a summary of authentic ebolavirus neutralization by cross-neutralizing human mAbs.

Table 8 shows $K_D$ values for recognition of EBOV GPΔTM by mature PE-87 bearing the indicated mutations in the CDR-H3 loop were determined by BLI. 95% confidence intervals are reported for each binding constant. $IC_{50}$ values for neutralization of rVSVs bearing ebolavirus GPs by mature PE-87 bearing the indicated mutations in the CDR-H3 loop.

Table 9 shows the mAb protection of mice after challenge with EBOV or SUDV.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned above and hereunder are incorporated herein by reference.

Definitions

As used herein, "neutralizing antibody" (NAb) refers to an antibody, for example, a monoclonal antibody, capable of disrupting a formed viral particle or inhibiting formation of a viral particle or prevention of binding to or infection of mammalian cells by a viral particle. As used herein, "diagnostic antibody" or "detection antibody" or "detecting antibody" refers to an antibody, for example, a monoclonal antibody, capable of detecting the presence of an antigenic target within a sample. As will be appreciated by one of skill in the art, such diagnostic antibodies preferably have high specificity for their antigenic target. As used herein, "human antibodies" refer to antibodies that were isolated from the B cells of a human or directly from the sequence of serum antibodies.

A "therapeutically effective" treatment refers a treatment that is capable of producing a desired effect. Such effects include, but are not limited to, enhanced survival, reduction in presence or severity of symptoms, reduced time to recovery, and prevention of initial infection. "Therapeutically effective" permutations of a mAb may enhance any of the above characteristics in a manner that is detectable by routine analysis of patient data. In certain embodiments, such therapeutically effective mutations include mutations that improve the stability, solubility, or production of the mAb, including mutations to the framework regions of the mAb sequence.

As used herein, 'immunoreactive fragment' refers in this context to an antibody fragment reduced in length compared to the wild-type or parent antibody which retains an acceptable degree or percentage of binding activity to the target antigen. As will be appreciated by one of skill in the art, what is an acceptable degree will depend on the intended use.

As used herein, a mAb has "pan-Ebola" binding characteristics if it is capable of binding to at least 2, but preferable more, ebolavirus species.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as kappa and lambda. Heavy chains are classified as gamma, mu, alpha, delta, or epsilon, and define the antibody's isotype as IgG, IgM, IgA, IgD and IgE, respectively. Within each isotype, there may be subtypes, such as $IgG_1$, $IgG_2$, $IgG_3$, $IgG_4$, etc. Within light and heavy chains, the variable and constant regions are joined by a "J" region of about 12 or more amino acids, with the heavy chain also including a "D" region of about 3 or more amino acids. The particular identity of constant region, the isotype, or subtype does not impact the present invention. The variable regions of each light/heavy chain pair form the antibody binding site.

Thus, an intact antibody has two binding sites. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with well known conventions [Kabat "Sequences of Proteins of Immunological Interest" National Institutes of Health, Bethesda, Md., 1987 and 1991; Chothia, et al., J. Mol. Biol. 196:901-917 (1987); Chothia, et al., Nature 342:878-883 (1989)].

In another embodiment of the invention, there are provided glycoengineered variants of the monoclonal antibodies that contain predominantly a single glycoform. These glycans can be GnGn ($GlcNAc_2$-$Man_3$-$GlcNAc_2$), mono- or di-galactosylated ($Gal_{(1/2)}$-$GlcNAc_2$-$Man_3$-$GlcNAc_2$) (hereinafter mono-galactosylated="G1", di-galactosylated="G2", and a combination of the two, in any proportion="G1/G2"), mono- or di-sialylated ($NaNa_{(1,2)}$-$Gal_{(1/2)}$-$GlcNAc_2$-$Man_3$-$GlcNAc_2$) containing little or no fucose or xylose. A predominantly single glycoform is any glycoform that represents more than half (e.g. greater than 50%, 60%, 70%, 80%, 90%, 95%, 96%, 97%, 98%, 99%) of all glycoforms present in the antibody solution.

The RAMP system has been used for glycoengineering of antibodies, antibody fragments, idiotype vaccines, enzymes, and cytokines. Dozens of antibodies have been produced in the RAMP system by Mapp (5, 6) and others (7, 8). These have predominantly been IgGs but other isotypes, including IgM (9, 10), have been glycoengineered. Glycoengineering has also been extended to human enzymes in the RAMP system (11, 12). Since the RAMP system has a rapid turn-around time from *Agrobacterium* infection to harvest and purification (13) patient specific idiotype vaccines have been used in clinical trials for non-Hodgkins lymphoma (7).

For glycoengineering, recombinant *Agrobacterium* containing a mAb cDNA is used for infection of *N. benthamiana* in combination with the appropriate glycosylation Agrobacteria to produce the desired glycan profile. For wild-type glycans (i.e. native, plant-produced glycosylation) wild-type *N. benthamiana* is inoculated with only the *Agrobacterium* containing the anti-M2e cDNA. For the GnGn glycan, the same *Agrobacterium* is used to inoculate plants that contain little or no fucosyl or xylosyl transfrases (ΔXF plants). For galactosylated glycans, ΔXF plants are inoculated with the *Agrobacterium* containing the mAb cDNA as well as an *Agrobacterium* containing the cDNA for β-1,4-galactosyltransferase expression contained on a binary *Agrobacterium* vector to avoid recombination with the TMV and PVX vectors (14). For sialylated glycans, six additional genes are introduced in binary vectors to reconstitute the mammalian sialic acid biosynthetic pathway. The genes are UDP-N-acetylglucosamine 2-epimerase/N-acetylmannosamine kinase, N-acetylneuraminic acid phosphate synthase, CMP-N-acetylneuraminic acid synthetase, CMP-NeuAc transporter, β-1,4-galactosylatransferase, and α2,6-sialyltransferase (14).

Glycanalysis of glycoengineered mAbs involved release of N-linked glycans by digestion with N-glycosidase F (PNGase F), and subsequent derivatization of the free glycan is achieved with anthranilic acid (2-AA). The 2-AA-derivatized oligosaccharide is separated from any excess reagent via normal-phase HPLC. The column is calibrated with 2-AA-labeled glucose homopolymers and glycan standards. The test samples and 2-AA-labeled glycan standards are detected fluorometrically. Glycoforms are assigned either by comparing their glucose unit (GU) values with those of the 2-AA-labeled glycan standards or by comparing with the theoretical GU values (15). Confirmation of glycan structure was accomplished with LC/MS.

While the RAMP system is an effective method of producing various glycoengineered and wild-type mABs, it will be recognized that other expression systems may be used to accomplish the same result. For example, mammalian cell lines (such as CHO or NSO cells [Davies, J., Jiang, L., Pan, L. Z., LaBarre, M. J., Anderson, D., and Reff, M. 2001. Expression of GnTIII in a recombinant anti-CD20 CHO production cell line: Expression of antibodies with altered glycoforms leads to an increase in ADCC through higher affinity for FCyRIII. Biotechnol Bioeng 74:288-294]), yeast cells (such as *Pichia pastoris* [Genigross T. Production of complex human glycoproteins in yeast. Adv Exp Med Biol. 2005; 564]) and bacterial cells (such as *E. Coli*) have been used produce such mABs.

Described herein are mAbs, designated PE-24, PE-87, PE-47, PE-16, PE-64 and PE-05, which have surprisingly exhibited pan-Ebola neutralizing characteristics. The preferred antibodies of the present invention comprise mAbs with amino acid sequences sufficiently identical to referenced amino acid sequences. By "sufficiently identical" is intended an amino acid sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs known in the art.

The sequences below show the amino acid modifications to mAb PE-64 VH and VL amino acids to yield mAb PE-47 (Modifications are shown in Bold, CDR sequences are Underlined).

mAb PE-64 VH amino acids:
SEQ ID No. 11
EVQLVESGGGLVKPGGSLRLSCAAS<u>GFTFSNAWMS</u>WVRQAPGKGLEWVGR

IKSKTDGGTIDYAAPVKGRFTISRDDSKNTVYLQMTSLKTEDTAVYYCTT

<u>YTEDMRYFDWLLRGGETFDY</u>WGQGTLVTVSS mAb PE-47 VH amino acids:
SEQ ID No. 12
EVQLVESGGGLVKPGGSLRLSCAAS<u>GFTFSNAWMS</u>WVRQAPGEGLEWVGR

IKSKTDGGTIDYAAPVKGRFTISRDDSKNTVYLQMTSLKTEDTAVYYCTT

<u>YTEDMQYFDWLLRGGETFDY</u>WGQGTLVTVSS

-continued mAb PE-64 VL amino acids:
SEQ ID No. 13
DIRLTQSPSSLSASVGDRVTITC<u>RASHYISTYLNW</u>YQQKPGKAPKLLIYA <u>ASNLQS</u>GVPSRFSGSGFGTDFSLTISSLQPEDFATYHC<u>QQSYSTPGRYTF</u>

<u>GQGTKVEIK</u> mAb PE-47 VL amino acids:
SEQ ID No. 14
DIQMTQSPSSLSASVGDRVTITC<u>RASQYISTYLNW</u>YQQKPGKAPKLLIYA <u>AYNLQS</u>GVPSRFSGSGSGTDFTLTISSLQPEDFATYYC<u>QQSYSTPGRYTF</u>

<u>GQGTKVEIK</u>

The antibodies displayed below were isolated from the peripheral B cells of a survivor of the 2014 Ebola virus outbreak in West Africa (CDR amino acids are disclosed in Table 1).

PE-87 VH amino acids: SEQ ID No. 15
PE-87 VH nucleotides: SEQ ID No. 16

An alternative PE-87 VH amino acid sequence is: SEQ ID No. 17 (alterations shown in Bold and Underlined)

EVQLVESGGGLVQPGGSLRVSCAASGFTFSSYAMSWVRQAPGKGLEWVSA

ISGLGGSTYYADSVKGRFTISRDNSKNTLYLQMNSLRAEDTAVYYCAKDH

RVWAAGYHFDYWGQGTLVTVSS

PE-87 VL amino acids: SEQ ID No.18
PE-87 VL nucleotides: SEQ ID No. 19

An alternative PE-87 VL amino acid sequence is: SEQ ID No. 20 (alterations shown in Bold and Underlined)

DIQMTQSPSTLSASVGDRVTITCRASQSISSWLAWYQQKPGEAPKLLISD

ASSLESGVPSRFSGSGSGTEFTLTISSLQPDDFATYYCQQYYSSPTFGGG

TKVEIK

PE-24 VH amino acids: SEQ ID No. 21
PE-24 VH nucleotides: SEQ ID No. 22
PE-24 VL amino acids: SEQ ID No. 23
PE-24 VL nucleotides: SEQ ID No. 24
PE-47 VH amino acids: SEQ ID No. 25
PE-47 VH nucleotides: SEQ ID No. 26
PE-47 VL amino acids: SEQ ID No.27
PE-47 VL nucleotides: SEQ ID No. 28
PE-16 VH amino acids: SEQ ID No.29
PE-16 VH nucleotides: SEQ ID No.30
PE-16 VL amino acids: SEQ ID No. 31
PE-16 VL nucleotides: SEQ ID No. 32
PE-05 VH amino acids: SEQ ID No. 33
PE-05 VH nucleotides: SEQ ID No.34
PE-05 VL amino acids: SEQ ID No. 35
PE-05 VL nucleotides: SEQ ID No. 36
PE-64 VH amino acids: SEQ ID No. 37
PE-64 VH nucleotides: SEQ ID No. 38
PE-64 VL amino acids: SEQ ID No. 39
PE-64 VL nucleotides: SEQ ID No. 40

TABLE 1

Amino acid residues comprising CDRs of anti-Ebola mAbs (SEQ ID Nos. indicated in parenthesis)

| Mab V region | CDR 1 | CDR 2 | CDR 3 |
|---|---|---|---|
| PE-87 VH | GFTFSSYAMS (41) | AISGLGGSTYYADSV (42) | DHRVWAAGYHFDY (43) |
| PE-87 VL | RASQSISSWLA (44) | DASSLES (45) | QQYYSSPT (46) |
| PE-24 VH | GFTFSSYAMS (47) | EISGLGGSTYYADSAK (48) | DHRVWAPGYYFDH (49) |
| PE-24 VL | RASQSISSWLA (50) | DASSLES (51) | QQYNRSPT (52) |
| PE-47 VH | GFTFSNAWMS (53) | RIKSKTDGGTIDYAAPVK (54) | YTEDMQYFDWLLRGGETFDY (55) |
| PE-47 VL | RASQYISTYLN (56) | AAYNLQS (57) | QQSYSTPGRYT (58) |
| PE-16 VH | GYTFTTYYMH (59) | IINPSGGITRYAQKFQ (60) | DRYPVLFATDYGMDV (61) |
| PE-16 VL | RASQSVSGYLA (62) | DASNRAT (63) | QQRSIWPPGVT (64) |
| PE-05 VH | GFTFGDYAMS (65) | FLRSKAYGGTAEYAASVK (66) | DGFRGSSWGYSYYGMDV (67) |
| PE-05 VL | SGSSSNIGGNTVS (68) | TNDQRPS (69) | WDDSLNGPVFGGGT (70) |
| PE-64 VH | GFTFSNAWMS (71) | RIKSKTDGGTIDYAAPVK (72) | YTEDMRYFDWLLRGGETFDY (73) |
| PE-64 VL | RASHYISTYLN (74) | AASNLQS (75) | QQSYSTPGRYT (76) |

In certain embodiments of the present invention, the above mAb sequences are affinity matured to enhance binding or otherwise improve the therapeutic efficacy of the antibody. In one embodiment, optimization of antibodies was performed via a light chain diversification protocol, and then by introducing diversities into the heavy chain and light chain variable regions as described below:

CDRL1 and CDRL2 selection: The CDRL3 of a single antibody was recombined into a premade library with CDRL1 and CDRL2 variants of a diversity of 1×10$^8$ and selections were performed with one round of MACS and four rounds of FACS. For each FACS round the libraries were affinity pressured using titrating amounts of an ebolavirus GP (for example, SUDV GP) and sorting was performed in order to obtain a population with the desired characteristics.

VH Mut selection: The heavy chain variable region (VH) was mutagenized via error prone PCR. The library was then created by transforming this mutagenized VH and the heavy chain expression vector into yeast already containing the light chain plasmid of the parent. Selections were performed similar to previous cycles using FACS sorting for two rounds. For each FACS round the libraries were affinity pressured using titrating amounts of Sudan GP and sorting was performed in order to obtain a population with the desired characteristics.

ADI-23774 (PE-47) was generated by combining the most improved HC (from the VH mut selection) with the most improved LC (from the L1/L2 selection).

Figure 1:
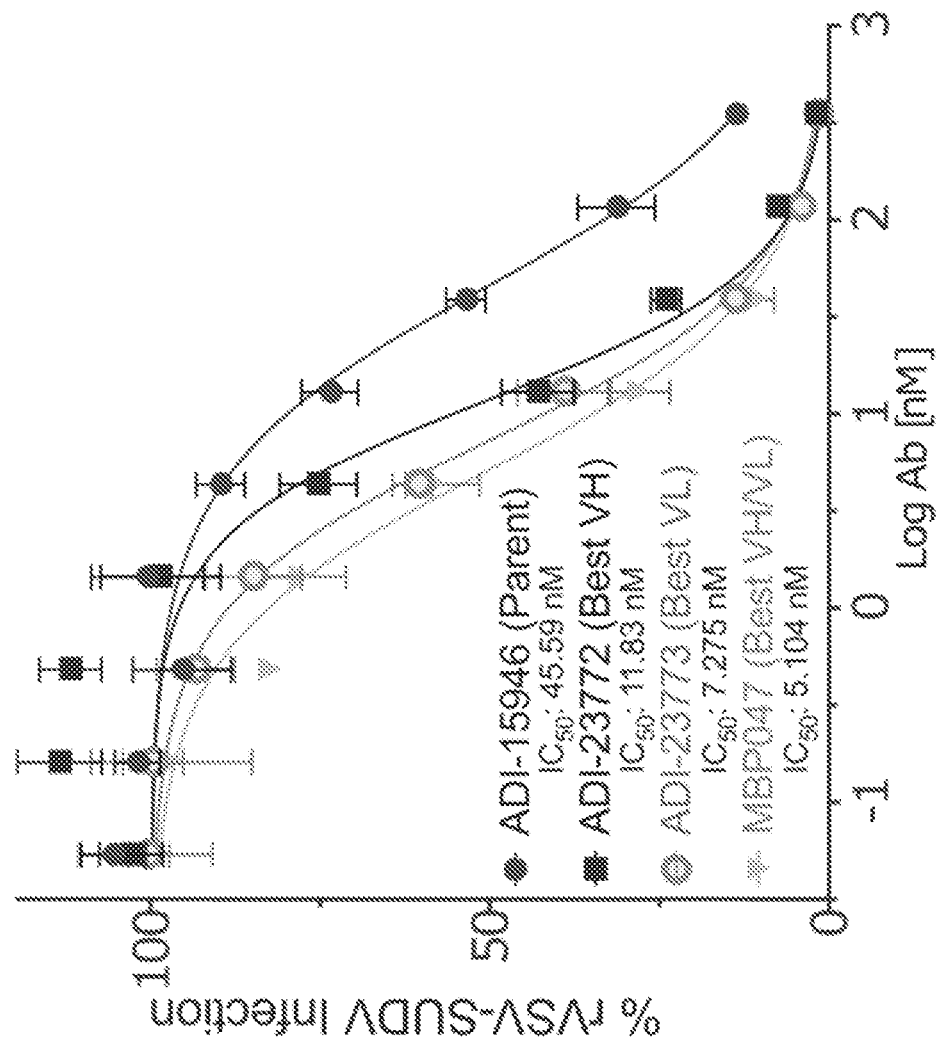
FIG. 1 shows a neutralization curve for affinity matured variants of one embodiment of the present invention.

FIG. 1 illustrates the enhanced neutralization potential of the parent (PE-64), best VH mutant, best VL mutant, and best VH/VL mutant (PE-47).

It will be apparent to those having skill in the art that these or alternate methods of affinity maturation may be used to rapidly and efficiently improve upon the desired characteristics of the mAb sequences described herein, and that routine analytical tools may be used to identify if any potential variant developed using these techniques possess the desired characteristic.

These antibodies have high affinity and avidity for Ebola glycoproteins, which means that in certain embodiments they can be used as therapeutic reagents administered to an individual with an ebolavirus infection or as prophylactic reagents to prevent an ebolavirus infection or as highly sensitive diagnostic tools. In particular, we have found that PE-87 and PE-47 act primarily at a step that follows GP→$GP_{CL}$ cleavage and receptor engagement. Endosomally generated $GP_{CL}$ species (either alone or in complex with NPC1) is the presumptive final target of these mAbs. Strikingly, GP cleavage to $GP_{CL}$ enhanced the antiviral potencies of PE-64, PE-87, and PE-47 by 50-200 fold. Together, these results suggest that the broadly neutralizing mAbs PE-87 and PE-47 differ from previously described monospecific mAbs (KZ52, c2G4, and 4G7), in their ability to target and neutralize a cleaved GP species that is generated deep in the endocytic pathway. Conversely, the latter mAbs appear to act principally at and/or prior to the GP→$GP_{CL}$ cleavage step. PE-64 displayed a dual behavior, and may act both upstream, to block GP cleavage, and downstream, to target one or more $GP_{CL}$-like species at or near the membrane fusion step. We assessed the protective efficacy of these broadly neutralizing human mAbs in three small-animal models of lethal ebolavirus challenge. First, wild type (WT) BALB/c mice were exposed to mouse-adapted EBOV (EBOV-MA), and then administered a single dose of each mAb at 2 days post-infection (300 μg/animal). Cross-neutralizing mAbs were highly (≥80%) protective against EBOV in this stringent post-exposure setting, with little or no weight loss apparent in mAb-treated animals.

Figure 2:
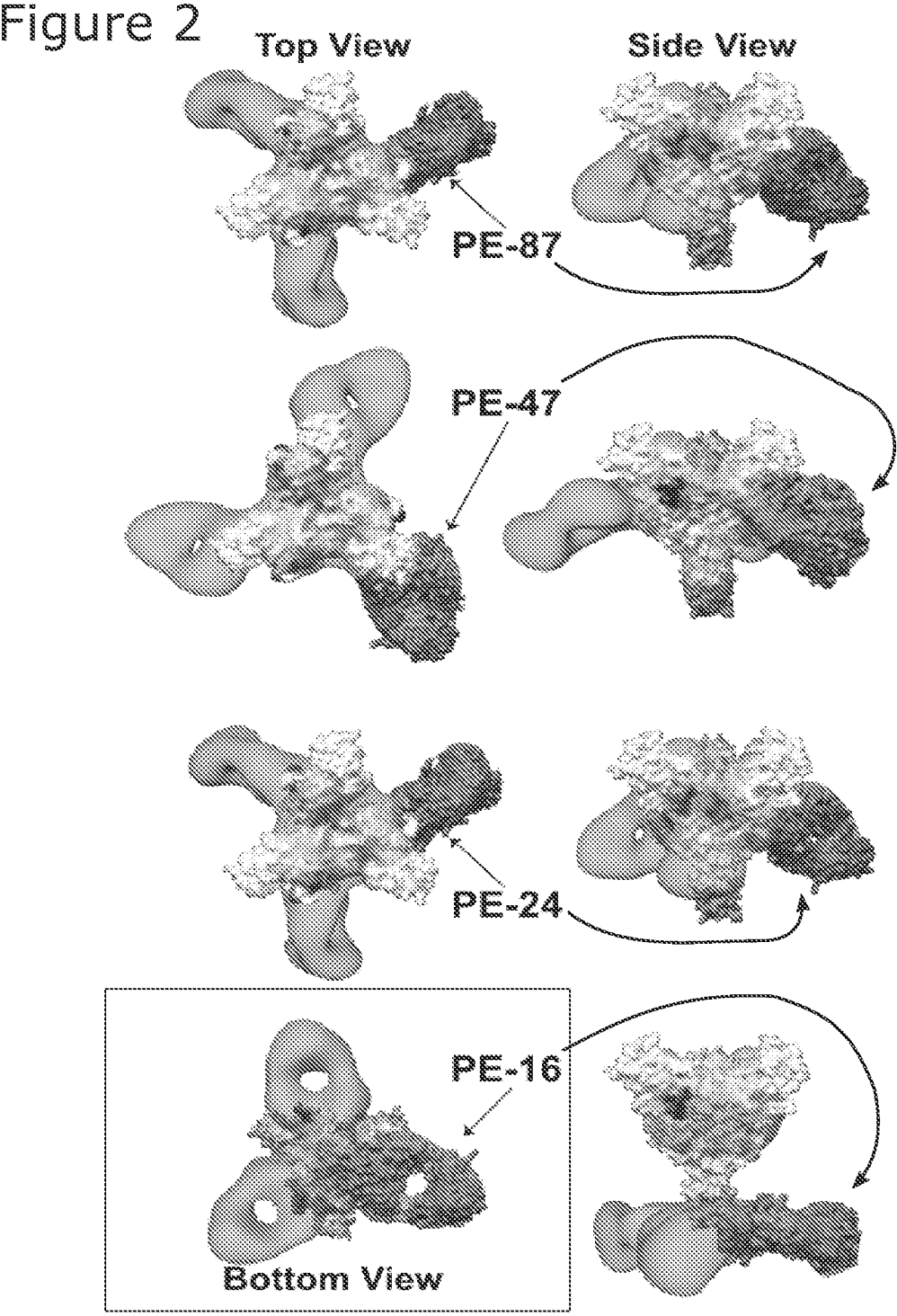
FIG. 2 shows the binding sites on the EBOV-GP of various embodiments of the monoclonal antibodies of the present invention.

FIG. 2 illustrates negative stain EM reconstructions of broadly neutralizing ebolavirus mAbs. A structure of ebolavirus GP (based on PDB IDs:5JQ3) displaying the antigenic surfaces and corresponding structural regions of interest. The disordered mucin domain (dashed lines), GP1, GP2, fusion loop, glycan cap in, CHR2 region and the N563-linked glycan. Top and side views are shown for negative stain EM 3D reconstructions of Fab models of PE-87, PE-47, PE-24 and PE-16 (shown in dark gray) in complex with EBOV GP.

We next evaluated the NAbs in the Type I interferon α/β receptor-deficient mouse model for SUDV challenge. Mice were exposed to WT SUDV, and then dosed with each NAb on days 1 and 3 post-infection (300 μg/animal/dose). The pan-ebolavirus mAbs PE-87 and PE-47 afforded ≥95% survival and greatly reduced weight loss, relative to the PBS control group. By contrast, PE-16 and PE-64, both weak SUDV neutralizers, provided little or no protection against SUDV.

Finally, we tested the anti-BDBV efficacy of the two pan-ebolavirus human mAbs, PE-87 and PE-47, in the domestic ferret, which is the only described non-NHP model for BDBV challenge. Animals received two doses of each NAb (15 mg and 10 mg per animal on days 3 and 6 post-challenge, respectively). As observed previously, BDBV infection was uniformly lethal, with PBS-treated animals succumbing between days 8-10 following challenge. By contrast, both mAbs afforded highly significant levels of survival (3 of 4 animals for PE-87; 2 of 4 for PE-24). Furthermore, peak viremia levels correlated with mAb treatment and survival outcome, with lower viral titers observed in the surviving animals relative to those that succumbed to infection (p<0.001), and in mAb-treated animals relative to PBS-treated controls (p<0.001). Viremia also trended lower in animals receiving PE-87 relative to those receiving PE-47, but this difference did not reach statistical significance. In sum, our findings demonstrate that the pan-ebolavirus mAbs PE-87 and PE-47 can afford post-exposure protection against challenge by the three divergent ebolaviruses currently associated with lethal disease outbreaks in humans.

In another embodiment of the present invention, the mAbs of the present invention have been shown to provide complete protection to a non-human primate model of Ebola virus challenge. Four days after exposure to a lethal challenge of EBOV virus, a group of rhesus macaque monkeys were treated with either one dose of an NAb cocktail (comprising 25 mg/kg each of PE-87 and PE-47) or two doses of the same NAb cocktail (one at 4 days post infection, comprising 50 mg/kg of the NAbs, and another at 7 days post infection, comprising 25 mg/kg of the NAbs). As previously observed, EBOV infection was uniformly lethal, with the all PBS-treated animals succumbing by the $7^{th}$ day post infection. By contrast, every animal from the NAb treatment groups survived, with no detectable viral RNA present in the blood of the treatment groups 10 days following the initial treatment, as assayed via qRT-PCR.

The NAb cocktail of PE-87 and PE-47 (also refered to herein as MBP134) was further tested as follows. First, escape mutants that were resistant to the individual components of MBP134 were generated. Escape mutant selections were performed by serial passage of rVSV-GP particles in the presence of test antibody. Briefly, serial 3-fold dilutions of virus were preincubated for one hour with a concentration of antibody corresponding to the $IC_{90}$ value derived from neutralization assays, and then added to confluent monolayers of Vero cells in 12-well plates, in duplicate. Infection was allowed to proceed to completion (>90% cell death by eye), and supernatants were harvested from the infected wells that received the highest dilution (i.e., the least amount) of viral inoculum. Following three subsequent passages under antibody selection with virus-containing supernatants as above, supernatants from passage 4 were tested for viral neutralization escape. If resistance was evident, individual viral clones were plaque-purified on Vero cells, and their GP gene sequences were determined as described previously (Wong et al., 2010).

Figure 3:
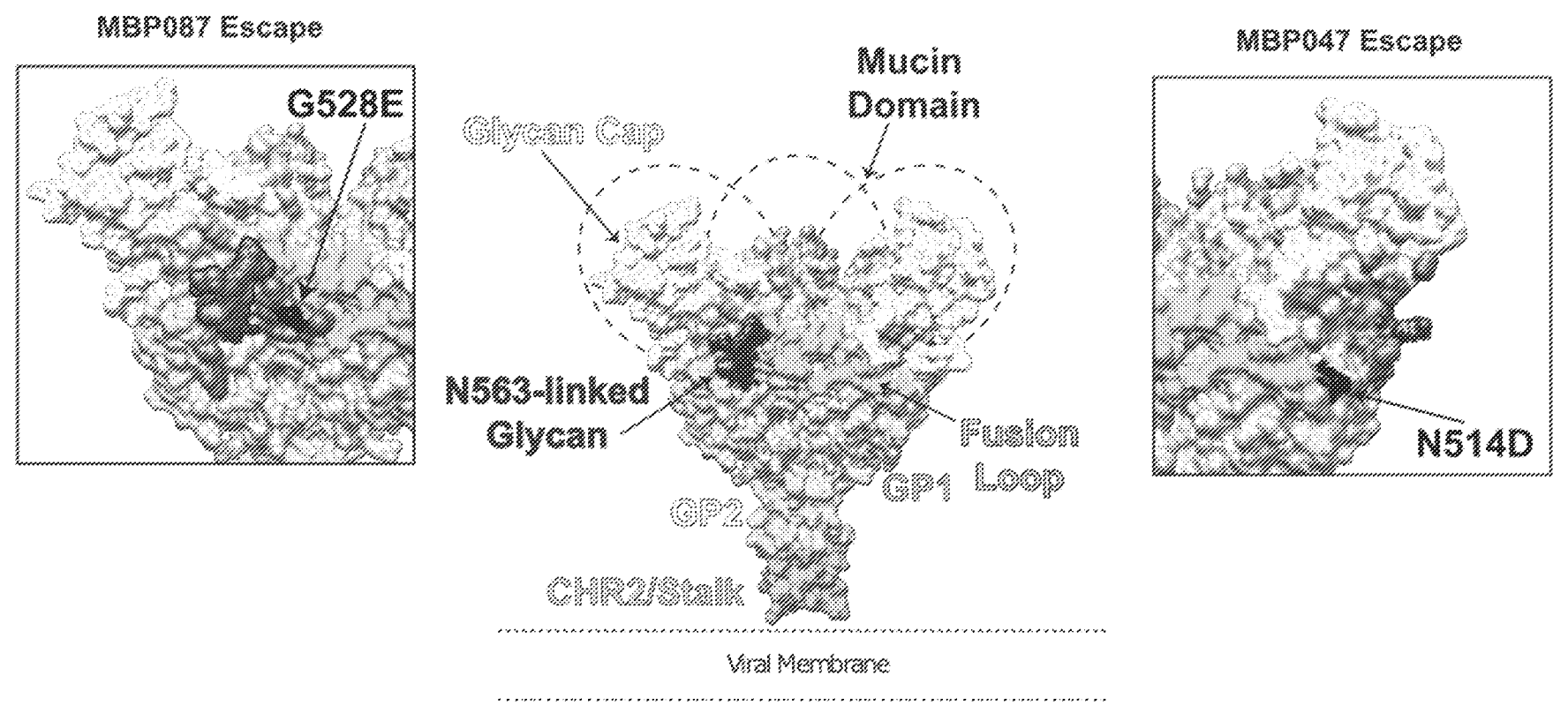

FIG. 3 illustrates the mutations to the rVSV-GP and their relative locations within the three-dimentional structure of the viral glycoprotein for the two escape mutants that were most resistant to PE-47 (MBP047) and PE-87 (MBP087) respectively. Namely, the PE-87 escape mutant contained a G528E substitution, while the PE-47 escape mutant contained a N514D substitution.

Figure 4:
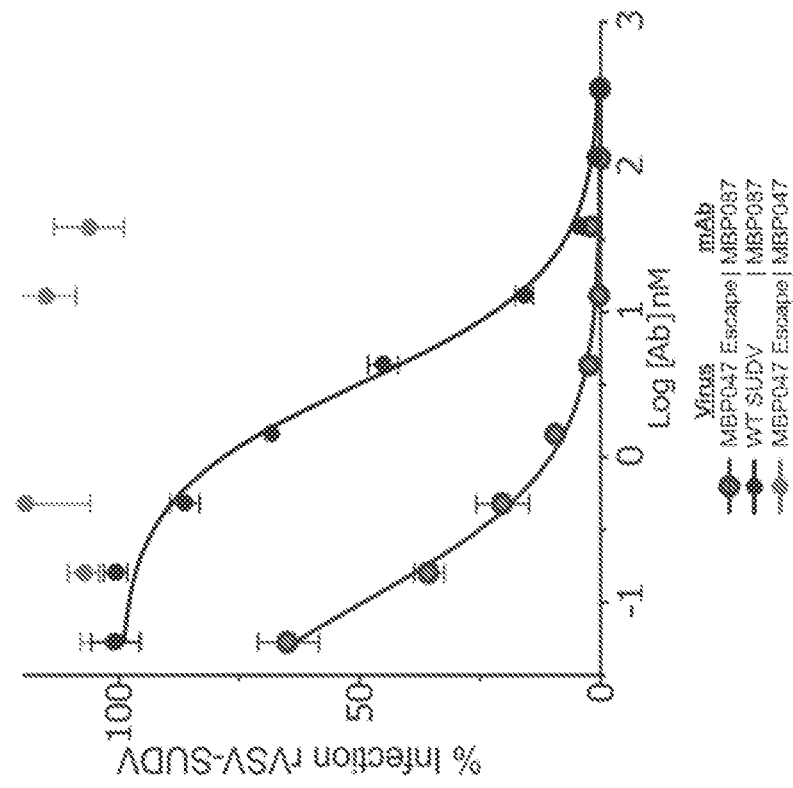
FIG. 4 shows neutralization assays preformed against the escape mutants.
Figure 4:
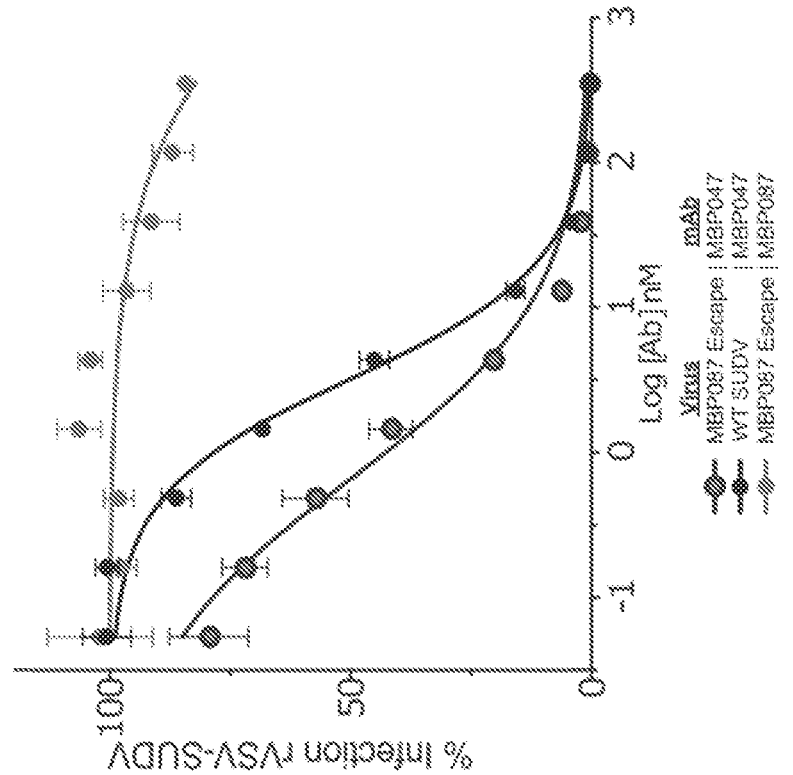

FIG. 4 illustrates the dose response curves of the above-mentioned escape mutants and the wild-type SUDV virus to concentrations PE-47 and PE-87. Importantly with regard to the efficacy of a multi-mAb cocktail, the escape mutations which provided resistance to one mAb resulted in significantly enhanced neurtralization by the other. As such, in certain embodiments of the present invention, a combination of multiple antibodies is provided which significantly reduce the risk of viral resistance development.

As noted above, antibodies comprising a substantially single glycan and lacking fucose show enhanced efficacy in patients. To determine if afucosylated MBP134 has increased efficacy in mammals, fucosylated and afucosylated versions of the cocktail were used to treat guinea pigs challenged with a lethal dose of EBOV. All guinea pigs were healthy and immune competent as per vendor's representation. All guinea pigs were drug and test naive. Animals were monitored daily for food and water consumption and given environmental enrichment according to the guidelines for the species. Cleaning of the animals was completed three times per week which included a complete cage and bedding material change. Animals were kept two or three per cage in the large shoe box cages from IVC Alternative Design. Each unit is ventilated with a HEPA blower system. 4-6 week old female Hartley guinea pigs (250-300 g) were randomly assigned to experimental groups and challenged via IP with a 1000×LD50 of guinea pig adapted EBOV/Mayinga in 1 mL of DMEM. Either MBP134 or the afucosylated MBP134-N was given IP at indicated time points and doses, with 6 guinea pigs/group (n=6). Control guinea pigs with 4 animals/group (n=4), were given PBS treatment. Animals were observed for clinical signs of disease, survival and weight change for 15-16 days, while survival was monitored for an additional 12 days.

Figure 5:
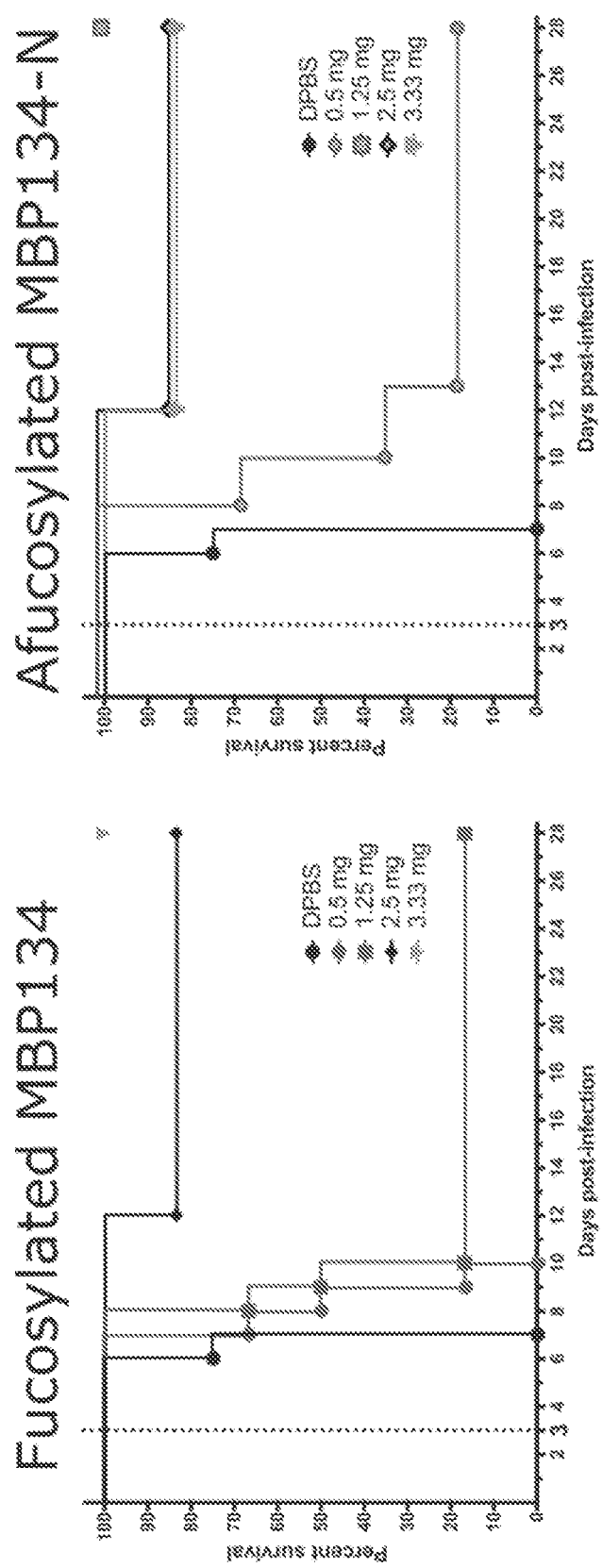
FIG. 5 shows survival data for ebolavirus infected guinea pigs treated with certain embodiments of the present invention.
Figure 6:
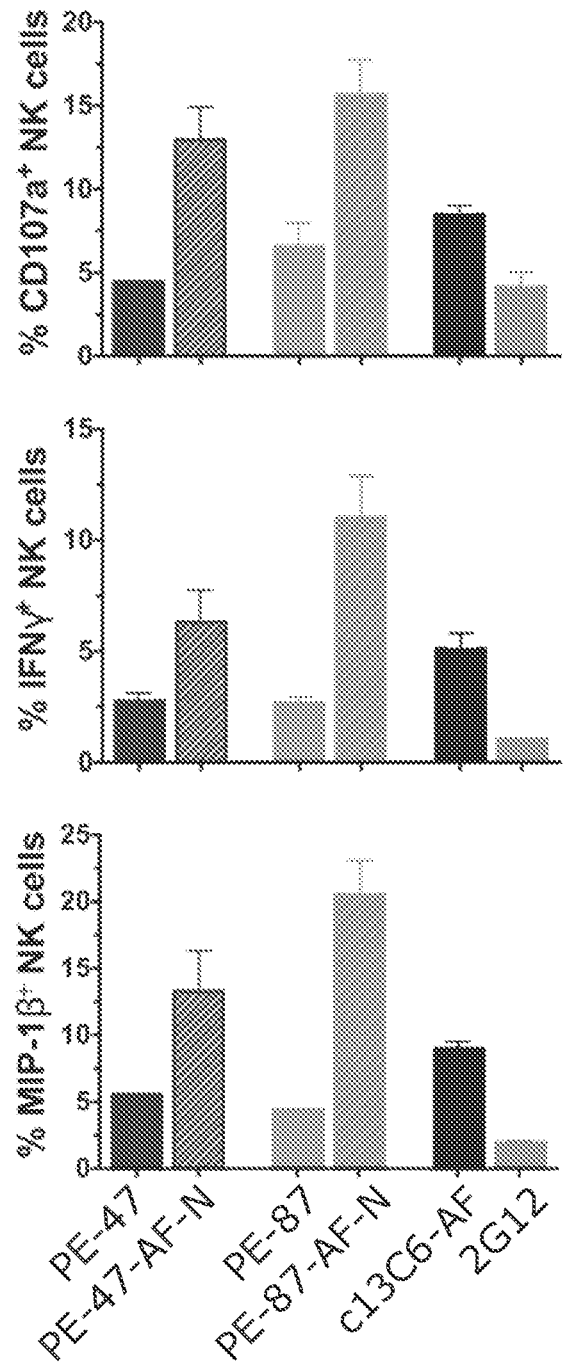
FIG. 6 shows immune system response data from ebolavirus infected guinea pigs treated with certain embodiments of the present invention.

FIG. 5 illustrates the survival curves of the afucosylated vs. fucosylated MBP134 at various doses. The afucosylated cocktail showed dramatically improved survival, even at the lowest dosage tested. Furthermore, blood drawn from the animals showed significantly increased immune reactions in response to treatment with afucosylated PE-47 and PE-87, as compared to their fucosylated counterparts and other anti-EBOV mAbs c13C6 (also afucosylated) and 2G12, as illustrated in FIG. 6. Thus, in certain embodiments of the present invention, there is provided a monoclonal antibody that substantially lacks fucose.

Figure 7:
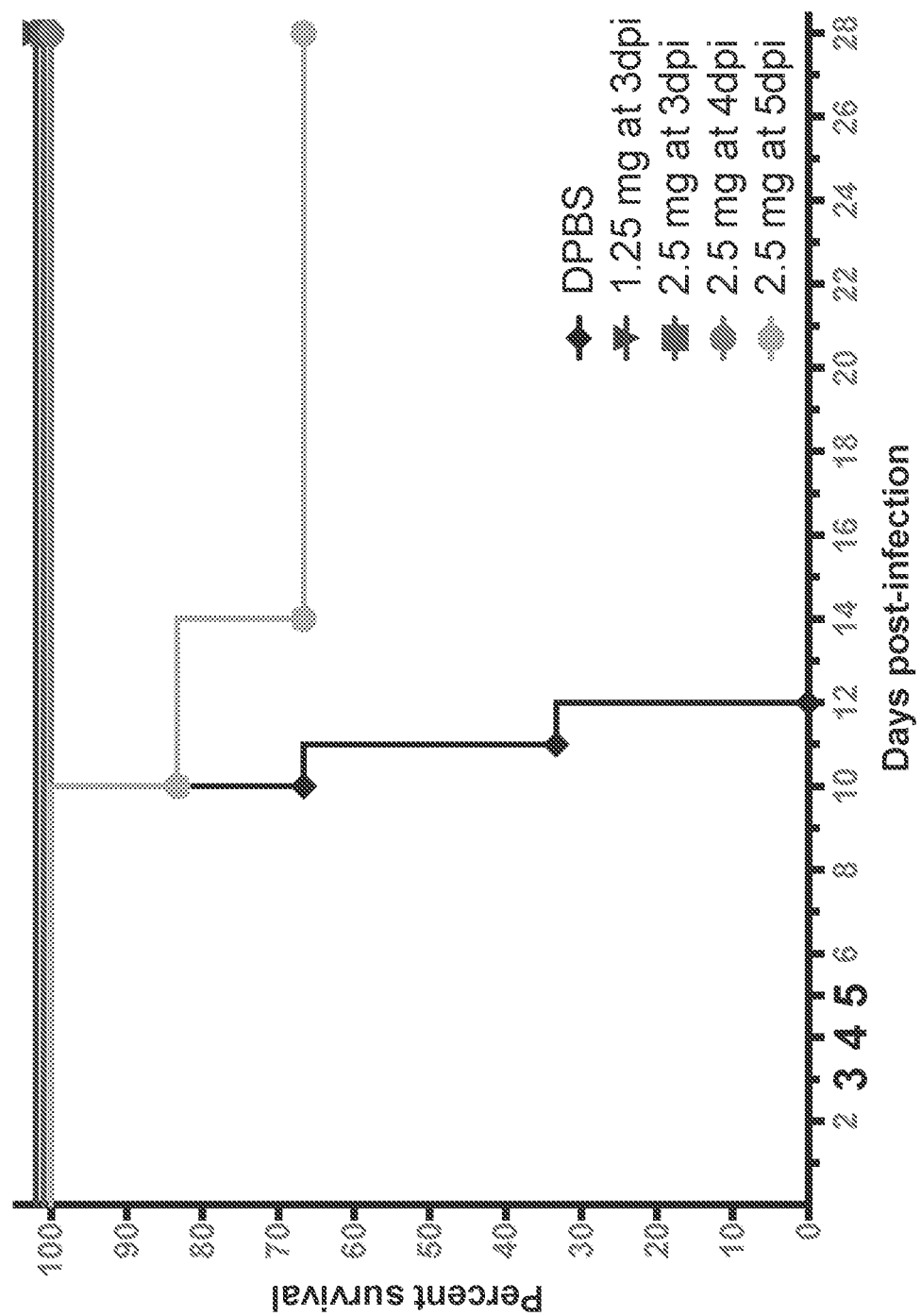
FIG. 7 shows survival data for ebolavirus infected guinea pigs treated with certain embodiments of the present invention.
Figure 8:
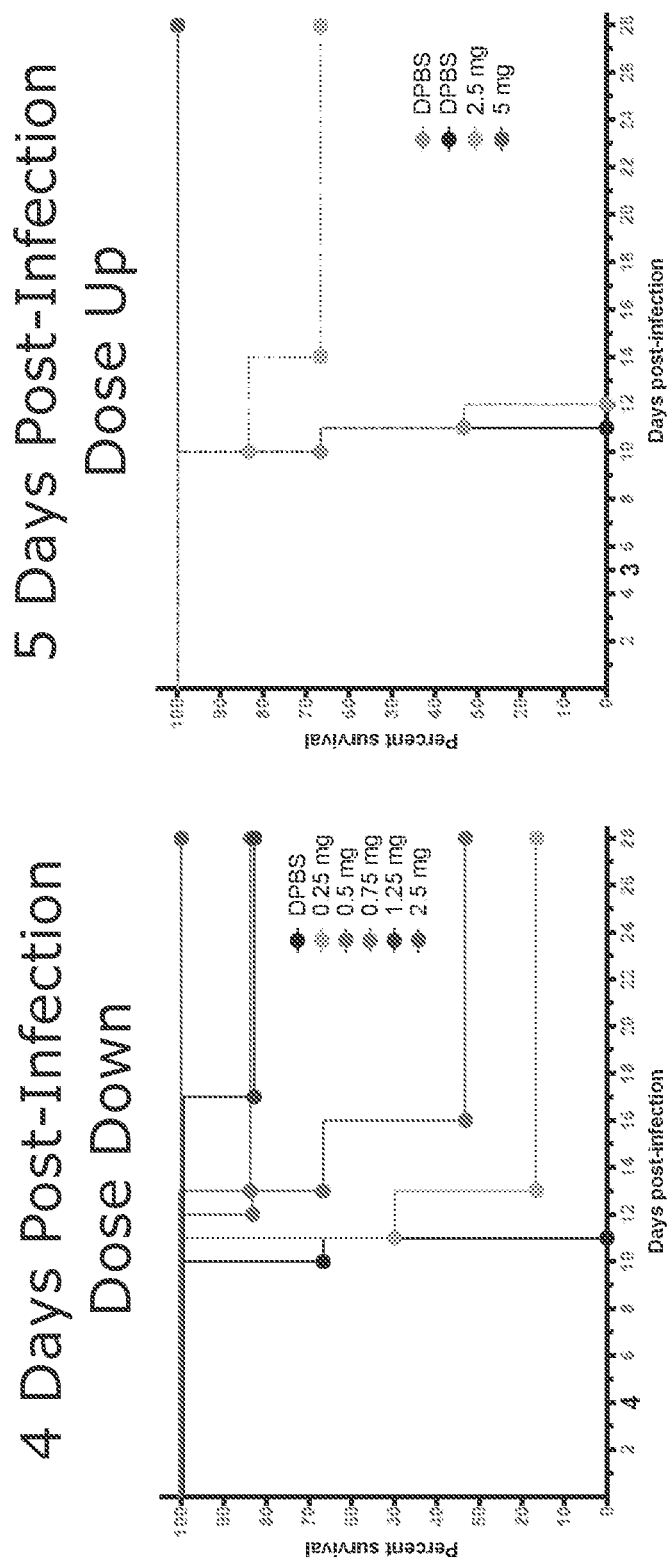
FIG. 8 shows survival data for ebolavirus infected guinea pigs treated with certain embodiments of the present invention.

To determine the ability of the afucoslyated MBP134 to neutralize multiple strains of the ebolavirus, a dose down study of guinea pigs infected with a lethal dose of SUDV was conducted. As illustrated in FIG. 7, animals treated at three and four days post infection had 100% survival, while even treatment at 5 dpi resulted in a dramatic increase in survival. To determine if a lower dose of MBP134 would be effective at 4 dpi, and if a higher dose would lead to increased survival if administered at 5 dpi, further tests were conducted. As illustrated in FIG. 8, reduced doses of MBP134 administered at 4 dpi resulted in excellent, though not perfect, survival rates among the treated animals. Furthermore, doubling the dose administered at 5 dpi resulted in all of the infected animals surviving. In certain embodiments of the present invention, the increase dosage of the monoclonal antibodies at later dates post infection allows the host animals to overcome the increased viral load associated with the infection.

Thus, in certain embodiments of the present invention, a patient is treated with an effective dose of a monoclonal antibody or combination of monoclonal antibodies. An effective dose includes, but is not limited to, 0.01 mg/kg, 0.05 mg/kg, 0.1 mg/kg, 0.25 mg/kg, 0.5 mg/kg, 0.75 mg/kg, 1 mg/kg, 2 mg/kg, 5 mg/kg, 10 mg/kg, 25 mg/kg, 50 mg/kg, and 100 mg/kg To further explore the ability of the monoclonal antibodies disclosed herein to protect against multiple strains of the ebolavirus in mammals, female ferrets were infected with various strains of ebolavirus and treated with different dosages of MBP134. Female ferrets weighing 0.75-1 kg were housed 2-3 per cage per study. Ferrets were anesthetized by intramuscular injection with a ketamine-acepromazine-xylazine cocktail prior to all procedures. Prior to challenge, transponder chips (Bio-Medic Data Systems) were subcutaneously implanted for identification and temperature monitoring. Subjects were challenged intranasally with a lethal dose of 1000 plaque-forming units (PFU) of ZEBOV strain Kikwit, SEBOV strain Gulu, or BDBV and treated with MBP134-N at the times and dosing shown in FIG. 9. As shown in FIG. 9, two doses of 15 mg at two or three dpi and five or six dpi were sufficient to offer full survival to the infected mammals. Furthermore, the results illustrated here, combined with those discussed above, indicate that the MBP134 cocktail provides protection against many different stains of ebolavirus in mammals.

To determine if this protection extends to primates, rhesus macaques were infected with a lethal dose of EBOV/Kikwit and treated with the monoclonal antibodies of the present invention. Rhesus macaques at UTMB were challenged by intramuscular injection (IM) with 1,000 PFU of EBOV/Kikwit. Two treatment groups (n=4/group) were treated either with a single 25 mg/kg dose of MBP134-N on day 4 or two doses of MBP134-N day 4 (50 mg/kg) and day 7 (25 mg/kg) post infection. Control animals (n=2) were treated with PBS. All the macaques were given physical examinations and blood was collected at the time of viral challenge; and on days 4, 7, 10, 14, 21, and 28 after challenge. The macaques were monitored daily and scored for disease progression with an internal Filovirus scoring protocol approved by the UTMB Institutional Animal Care and Use Committee (IACUC) in accordance with state and federal statutes and regulations relating to experiments involving animals and by the UTMB Institutional Biosafety Committee. The scoring changes measured from baseline included posture/activity level; attitude/behavior; food and water intake; weight; respiration; and disease manifestations, such as visible rash, hemorrhage, ecchymosis, or flushed skin, with increased scores resulting in euthanasia. As illustrated in FIG. 10, all of the treated primates survived the lethal challenge of ebolavirus.

As illustrated in FIG. 11, the protection offered to primates by the antibodies of the present invention extends to multiple strains of ebolavirus. Even a single dose of MBP134 is sufficient to protect from a lethal challenge of both SUDV/Nza-Boniface and SUDV/Gulu in rhesus macaques.

Furthermore, the monoclonal antibodies of the present invention provide protection from ebolavirus challenge in different species of primate. Cynomolgus monkeys at UTMB were challenged by intramuscular injection (IM) with 1,000 PFU of BDBV (200706291 Uganda isolate, Vero E6 passage 2). One treatment group (n=6) was treated with a single 25 mg/kg dose of MBP134 (from CHOK1-AF) on day 7 post infection via IV infusion. Control animals (n=3) were untreated. All the animals were given physical examinations and blood was collected at the time of viral challenge; and on days 4, 7, 10, 14, 21, and 28 after challenge (or at time of euthanasia). All animals were monitored daily and scored for disease progression with an internal filovirus scoring protocol approved by the UTMB Institutional Animal Care and Use Committee. The scoring changes measured from baseline included posture/activity level, attitude/behavior, food intake, respiration, and disease manifestations such as visible rash, hemorrhage, ecchymosis, or flushed skin. A score of ≥9 indicated that an animal met criteria for euthanasia. As illustrated in FIG. 12, a single dose of MBP134 as late as one-week post infection is sufficient to offer excellent protection.

In order to optimize the production methodology of the monoclonal antibodies disclosed herein, the ability of PE-87 and PE-47 produced in plants or CHO cells to neutralize numerous strains of ebolavirus were tested. As illustrated in FIG. 13, monoclonal antibodies produced in both plant and CHO based systems possess similar neurtralization characteristics. As such, these, or other systems known in the art, may be used to produce the monoclonal antibodies of the present invention.

It is of note that as discussed herein, any of the above described antibodies may be formulated into a pharmaceutical treatment for providing passive immunity for individuals suspected of or at risk of developing hemorrhagic fever comprising a therapeutically effective amount of said antibody. The pharmaceutical preparation may include a suitable excipient or carrier. See, for example, Remington: The Science and Practice of Pharmacy, 1995, Gennaro ed. As will be apparent to one knowledgeable in the art, the total dosage will vary according to the weight, health and circumstances of the individual as well as the efficacy of the antibody. While the preferred embodiments of the invention have been described above, it will be recognized and understood that various modifications may be made therein, and the appended claims are intended to cover all such modifications which may fall within the spirit and scope of the invention.

Materials and Methods 1

Human Subjects

Human blood samples were collected after Institutional Review Board (IRB) approval of a protocol to isolate B cells from healthy adult volunteers to identify antibodies elicited from prior immunization or infections. Eligible subjects were determined based on immunization and infection history recorded on a self-reported questionnaire completed prior to sample collection. Peripheral blood mononuclear cells were obtained from a survivor of the 2014 EBOV outbreak three months after the patient had been diagnosed with EBOV infection.

B Cell and Plasma Isolation

Approximately 85 ml of whole blood was collected in 8.5 ml ACD Solution A VACUTAINER® venous blood collection tubes (Becton Dickinson) per the manufacturer's protocol. Blood was transported at room temperature and distributed into 50 ml conical tubes before addition of 300 µl of ROSETTESEP™ human B cell enrichment cocktail (StemCell Technologies) per 21 ml of blood, mixed by inversion and incubated for 20 minutes at room temperature. The total volume was brought to 50 ml with Hank's Balanced Salt Solution (HBSS), layered over Ficoll-Paque Plus (GE Healthcare) and centrifuged following the manufacturer's protocol. The B cell layer was removed from the density gradient by pipette, washed twice in HBSS by centrifugation at 400×g, frozen at 6.5×106 cells/ml in a 1:1 mixture of FBS (Life Technologies) and cryoprotective medium (Lonza) and stored under liquid nitrogen. Plasma was collected from the top layer of the density gradient and stored at −80° C. until use.

TABLE 2

Efficiency of anti-GP mAb isolation from peripheral B cells.

| | |
|---|---|
| Total number of IgG+ B cells sorted: | 600 |
| Number of antibodies cloned: | 420 (70%) |
| Number of clones expressing IgG: | 378 (63%) |
| Number of EBOV GP binders: | 349 (58%) |

Anti-EBOV GP Plasma ELISA

A high-binding ELISA plate was coated with 1 µg/ml of EBOV rGPΔTM (IBT BioSciences) diluted in PBS overnight at 4° C. After washing, wells were blocked with 1% BSA in PBS and 0.05% Tween-20 for 2 hours at room temperature. Wells were washed and serial dilutions of human plasma (diluted in blocking buffer) were added and incubated for 1.5 hours at room temperature. As positive and negative controls, serial dilutions of mAb KZ52 (IBT BioSciences) or an irrelevant human mAb, respectively, were added to appropriate wells. After washing, HRP-conjugated donkey anti-human IgG (Jackson ImmunoResearch) or HRP-conjugated goat anti-human IgA (Southern Biotech) secondary antibody was incubated in appropriate wells for 1.25 hours at room temperature. Wells were washed twice and developed with SureBlue TMB substrate (KPL). The reaction was stopped with 1M HCl and wells were read on an EMax Microplate Reader (Molecular Devices) at 450 nm wavelength. Plasma endpoint titers were determined by calculating the highest serum dilution that gives a reading above the blank including three standard deviations.

Single B Cell Sorting

Purified B cells were stained using anti-human IgM (BV605), IgD (BV605), IgG (BV421), CD8 (APC-Cy7), CD14 (AF700), CD19 (PerCP-Cy5.5), CD20 (PerCP-Cy5.5) and biotinylated EBOV GPΔ™. Biotinylated GPΔTM was used at a concentration of 50 nM and detected using streptavidin-APC (Life Technologies) at a dilution of 1:500. Single cells were sorted on a MoFlo cytometer (Beckman-Coulter) into 96-well PCR plates (BioRad) containing 20 µl/well of lysis buffer [5 µl of 5× first strand cDNA buffer (Invitrogen), 0.5 µl RNaseOUT (Invitrogen), 1.25 µl dithiothreitol (Invitrogen), 0.625 µl NP-40 (New England Biolabs), and 12.6 µl dH2O]. Plates were immediately frozen on dry ice before storage at −80° C.

Amplification and Cloning of Antibody Variable Genes

Single B cell PCR was performed essentially as previously described [27]. Briefly, IgH, Igλ and Igκ variable gene transcripts were amplified by RT-PCR and nested PCR reactions using cocktails of primers specific for IgG [27]. The primers used in the second round of PCR contained 40 base pairs of 5' and 3' homology to the cut expression vectors to allow for cloning by homologous recombination into Saccharomyces cerevisiae [28]. PCR products were cloned into S. cerevisiae using the lithium acetate method for chemical transformation [29]. Each transformation reaction contained 20 µl of unpurified heavy chain and light chain PCR product and 200 ng of cut heavy and light chain plasmids. Individual yeast colonies were picked for sequencing and down-stream characterization.

Expression and Purification of Antibodies and Fab Fragments

Antibodies used for binding experiments, competition assays, neutralization assays, and structural studies were expressed in Saccharomyces cerevisiae cultures grown in 24 well plates. After 6 days of growth, the yeast cell culture supernatant was harvested by centrifugation and subject to purification. IgGs used in protection experiments were expressed by transient co-transfection of heavy and light chain plasmids into HEK293 cells. One day prior to transfection, HEK293 cells were passaged at 2.0-2.5×106 cells/ml. On the day of transfection, cells were pelleted by centrifuging at 400 g for 5 min, and cell pellets were resuspended in fresh FreeStyle F17 medium at a density of 4×106 cells/ml and returned to the incubator. A transfection mixture was prepared by first diluting the plasmid DNA preparations in FreeStyle F17 medium (1.33 µg total plasmid DNA per ml of culture). Transfection agent, PEIPRO™ (Polyplus Transfection, Illkirch, France), was then added to the diluted DNA at a DNA-to-PEI ratio of 1:2, and the mixture was incubated at room temperature for 10 min. The transfection mixture was then added to the culture. Cultures were harvested six days post transfection by two rounds of centrifugation, each at 2000×g for 5 min, and the clarified conditioned medium subject to antibody purification. Cell supernatents were purified by passing over Protein A agarose (MAB SELECT SURE™ from GE Healthcare Life Sciences). The bound antibodies were washed with PBS, eluted with 200 mM acetic acid/50 mM NaCl pH 3.5 into 1/8$^{th}$ volume 2M Hepes pH 8.0, and buffer-exchanged into PBS pH 7.0. Fabs were generated by digesting the IgGs with papain for 2 h at 30° C. The digestion was terminated by the addition of iodoacetamide, and the Fab and Fc mixtures were passed over Protein A agarose to remove Fc fragments and undigested IgG. The flowthrough of the Protein A resin was then passed over CAPTURESELECT™ IgG-CH1 affinity resin (ThermoFischer Scientific), and eluted with 200 mM acetic acid/50 mM NaCl pH 3.5 into 1/8th volume 2M Hepes pH 8.0. Fab fragments then were buffer-exchanged into PBS pH 7.0.

Expression and Purification of EBOV GPs

Recombinant EBOV GP ectodomains containing the mucin-like domain (EBOV GPΔ™) or lacking residues 312-463 of the mucin-like domain (EBOV GPΔmuc) were produced as described previously [10, 30].

EBOV GPΔTM Biotinylation

EBOV GPΔTM was biotinylated using EZ-LINK™ Sulfo-NHS-LC-Biotin (Life Technologies) followed by a desalting step by a ZEBA™ Spin Desalting Column (Life Technologies).

Biolayer Interferometry Binding Analysis

IgG binding to the different GP antigens was determined by BLI measurements using a ForteBio Octet HTX instrument (Pall Life Sciences). For high-throughput KD screening, IgGs were immobilized on AHQ sensors (Pall Life Sciences) and exposed to 100 nM antigen in PBS containing 0.1% BSA (PBSF) for an association step, followed by a dissociation step in PBSF buffer. Data was analyzed using the ForteBio Data Analysis Software 7. The data was fit to a 1:1 binding model to calculate an association and dissociation rate, and KD was calculated using the ratio kd/ka.

Anti-GP mAb ELISAs

ELISA plates were coated with 50 µl PBS containing 4 µg/mL EBOV GP antigens for 1 h at room temperature. After washing, wells were blocked with 3% BSA for 1 h at room temperature. After removal of the blocking solution, mAbs were applied to the plates at a concentration of 0.2 µg/ml and incubated at room temperature for 1 h. After washing, binding was detected with an anti-human HRP-conjugated secondary antibody and TMB substrate. Optical density was read at 450 nm.

TABLE 3

| Cross-reactivity of pan ebolavirus mAbs (elisa) | | | | | | | |
|---|---|---|---|---|---|---|---|
| mAb | EBOV | SUDV | BDBV | RESTV | TAFV | MARV | sGP | GPcl |
| PE-24 | YES | YES | YES | YES | YES | NO | NO | YES |
| PE-05 | YES | YES | YES | YES | YES | NO | YES | NO |
| PE-87 | YES | YES | YES | YES | YES | NO | NO | YES |
| PE-16 | YES | WEAK | YES | NO | YES | NO | NO | YES |
| PE-47 | YES | YES | YES | NP | YES | NO | NO | YES |

Antibody Competition Assays

Antibody competition assays were performed essentially as previously described [31]. Antibody competition was measured by the ability of a control anti-EBOV GP Fab to inhibit binding of yeast surface-expressed anti-GP IgGs to GPΔmuc. 50 nM biotinylated GPΔmuc was pre-incubated with 1 µM competitor Fab for 30 min at RT and then added to a suspension of yeast-expressed anti-GP IgG. Unbound antigen was removed by washing with PB SF. After washing, bound antigen was detected using Streptavidin Alexa Fluor 633 at a 1:500 dilution (Life Technologies) and analyzed by flow cytometry using a BD FACS Canto II. Results are expressed as the fold reduction in antigen binding in the presence of competitor Fab relative to an antigen-only control.

Neutralization Assays

Virus-specific neutralizing antibody responses were titrated essentially as previously described [32]. Briefly, plasma or antibodies were diluted serially in Minimal Essential Medium (Corning Cellgro, Manassas, Va.) containing 5% heat-inactivated fetal bovine serum (Gibco-Invitrogen, Gaithersburg, Md.), 1× Anti-Anti (Gibco-Invitrogen, Gaithersburg, Md.) (MEM complete) and incubated 1 hour at 37° C. with virus. After incubation, the antibody-virus or plasma-virus mixture was added in duplicate to 6-well plates containing 90-95% confluent monolayers of Vero E6 cells. Plates were incubated for 1 hour at 37° C. with gentle rocking every 15 minutes. Following the incubation, wells were overlaid with 0.5% agarose in supplemented EBME media, 10% heat-inactivated fetal bovine serum (Gibco-Invitrogen, Gaithersburg, Md.), 2× Anti-Anti (Gibco-Invitrogen, Gaithersburg, Md.), and plates were incubated at 37° C., 5% CO2 for 7 days. On day 7, cells were stained by the addition of a second overlay prepared as above containing 4-5% neutral red. Plates were incubated for 18-24 hours at 37° C., 5% CO2. The endpoint titer was determined to be the highest dilution with a 50% or greater or 80% or greater reduction (PRNT50, PRNT80) in the number of plaques observed in control wells. The assay limit of detection was calculated to be 5 plaque forming units (p.f.u.)/ml by this method.

TABLE 4

Candidate pan-Ebolavirus mAbs in vitro activity

| mAb | Epitope | Affinity (KD, nM) | Neutralization (VSV-GP IC$_{50}$, nM) | | | | | | Neut. WT EBOV PRNT$_{50}$ (nM) | Microneut. WT IC$_{50}$ (nM) | | |
|---|---|---|---|---|---|---|---|---|---|---|---|---|
| | | | EBOV | SUDV | BDBV | RESTV | TAFV | EBOV GP$_{CL}$ | | EBOV | SUDV | BDBV |
| PE-05 | GC | 44 | 8.8 | 34 | 3.7 | 22 | 0.8 | NR | 4.0 | 7.7 | NR | NR |
| PE-87 | IFL | <0.01 | 0.5 | 0.3 | 0.5 | 0.2 | 1.0 | 0.2 | <0.05 | 0.3 | 0.3 | 0.4 |
| PE-16 | Stalk | 0.16 | 0.2 | NR | 0.6 | NR | 4.8 | 5.7 | <0.02 | 0.05 | NR | 0.2 |
| PE-47 | Other | 3.5 | 6.6 | 5.1 | 0.4 | NR | 6.1 | 0.08 | NT | 0.7 | <0.1 | 0.5 |
| PE-24 | IFL | 1 | 1.8 | 0.5 | 0.8 | 0.2 | 1.5 | 0.6 | 0.4 | 1 | 0.4 | 0.3 |

Epitope analyses and affinity measurements were performed by both Mapp and Integrated BioTherapeutics. VSV-GP assays were performed in Dr. K. Chandran's laboratory (Albert Einstein); neutralization assays with wildtype virus were performed in Dr. J. Dye's lab (USAMRIID); IFL = internal fusion loop; GC = glycan cap; RBS = receptor binding site; GPCL = cleaved GP, the form of GP exposed in the endosome when virus is internalized by the cell in preparation for fusion with the host cell receptor; P = in progress; NR = non-reactive; NT = not tested; WT = wildtype.

Single-Particle Electron Microscopy

For all EM studies the EBOV GPΔTM construct described above was used. Fabs were generated as described above and incubated with the EBOV GPΔTM trimer at a ratio of 1:10 for overnight at 4° C. Complexes were then deposited onto a carbon coated copper mesh grid and stained with 1% uranyl formate. Samples were imaged on a Tecnai F12 microscope using the automated image acquisition software Leginon [33]. Images were collected at 52,000× magnification resulting in a final pixel size at the specimen level of 2.05 A using a Tietz 4K CMOS detector. Images were automatically uploaded to and processed within our Appion database [34]. Individual complexes were extracted from raw images using DogPicker [35] binned by 2 and placed into a stack. The stack was then subjected to reference free 2 dimensional classification using MRA/MSA [PMID 14572474]. Class averages that did not respond to Fab-EBOVΔ™ complexes were removed from all subsequent analyses. A subset of 2D class averages was used to create an initial model using common lines within EMAN2 [36]. The raw particle stack was then refined against the initial model using EMAN2 to yield the final 3D volumes. UCSF Chimera was used for modeling and figure generation [37].

EBOV Challenge Studies in Mice

The lethal mouse-adapted EBOV mouse model was developed at the U.S. Army Medical Research Institute of Infectious Diseases (USAMRIID) by serial passages of EBOV (Zaire) in progressively older suckling mice [38]. Female BALB/c mice, aged 6 to 8 weeks, were purchased from Charles River Laboratory. Upon arrival, mice were housed in microisolator cages in an animal biosafety level 4 containment area and provided chow and water ad libitum. On day 0, mice were infected intraperitoneally (i.p.) with 100 p.f.u. of mouse-adapted EBOV. Two days post-infection, groups of mice (10 mice per group) were treated i.p. with a single dose (100 μg) of antibody. Negative control mice received PBS. Mice were monitored daily (twice daily if there were clinical signs of disease) for 28 days post-infection. Group weights were taken on days 0-14, and on days 21 and 28 post-infection. Survival was compared using the log-rank test in GraphPad PRISM 5. Differences in survival were considered significant when the P value was less than 0.05. Research was conducted under an IACUC approved protocol in compliance with the Animal Welfare Act, PHS Policy, and other Federal statutes and regulations relating to animals and experiments involving animals. The facility where this research was conducted is accredited by the Association for Assessment and Accreditation of Laboratory Animal Care, International and adheres to principles stated in the Guide for the Care and Use of Laboratory Animals, National Research Council, 2011.

TABLE 5

Therapeutic efficacy of mAbs in a mouse model of EBOV infection.

| Treatment group[#] | No. survivors/total | Average weight loss (%)* | P value | mAb competition group |
|---|---|---|---|---|
| PBS | 2/10 | 8.8 | N/A | N/A |
| 2G4 | 4/10 | 7.2 | 0.095 | KZ52 competitor |
| ADI-15956 | 7/10 | 8.6 | 0.008 | HR2 |
| PE-16 | 7/10 | 9.1 | 0.008 | HR2 |
| ADI-15974 | 8/10 | 8.0 | 0.002 | HR2 |
| ADI-15758 | 8/10 | 9.8 | 0.009 | HR2 |
| ADI-15999 | 10/10 | 8.1 | <0.0001 | HR2 |
| ADI-15 820 | 6/10 | 9.9 | 0.026 | HR2 |
| ADI-15848 | 7/10 | 8.2 | 0.008 | HR2 |
| ADI-15960 | 5/10 | 15.4 | 0.073 | Undefined |
| ADI-15903 | 4/10 | 8.4 | 0.079 | Undefined |
| ADI-15959 | 5/10 | 8.4 | 0.040 | Undefined |
| ADI-15765 | 4/10 | 5.9 | 0.102 | Undefined |
| ADI-15818 | 3/10 | 13.8 | 0.164 | KZ52 competitor |
| PE-87 | 8/10 | 10.4 | 0.005 | KZ52 competitor |
| ADI-15734 | 6/10 | 7.3 | 0.026 | KZ52 competitor |
| ADI-15784 | 8/10 | 9.1 | 0.002 | KZ52 competitor |
| ADI-15772 | 7/10 | 11.8 | 0.011 | KZ52 competitor |
| PE-24 | 10/10 | 10.5 | 0.0003 | KZ52 competitor |
| ADI-15731 | 4/10 | 9.2 | 0.059 | 13C6 competitor |
| ADI-15932 | 4/10 | 12.1 | 0.139 | 13C6 competitor |
| ADI-15940 | 4/10 | 11.0 | 0.059 | 13C6 competitor |
| ADI-15 744 | 4/10 | 12.3 | 0.095 | 13C6 competitor |
| ADI-16037 | 8/10 | 7.0 | 0.005 | 13C6 competitor |
| ADI-16044 | 2/10 | 9.9 | 0.263 | 13C6 competitor |
| ADI-15817 | 4/10 | 9.9 | 0.095 | 13C6 competitor |
| PE-47 | 9/10 | 10.1 | 0.006 | Undefined |
| PE-05 | 9/10 | 8.2 | 0.008 | Undefined |

[#]Mice were given 100 vg of the indicated antibody, or PBS, two days post infection.
*Average weight change from the pre-injection baseline to the peak of clinical disease. Mice were weighed as groups.

SUDV Challenge Studies in Mice 4-5 week old, IFNa/bR KO mice will be inoculated I.P. with SUDV (1000 pfu). Experimental group will be treated with mAbs (0.3 ml volume) at indicated dose on days 1 and 4 post-infection. Control mice will vehicle control I.P. (0.3 ml volume) on the same schedule as experimental mice. Mice will be observed daily for 21 days for moribund condition. Moribund mice will be promptly euthanized (IAW SOP AC-11-07) when they meet euthanasia criteria (score sheet).

Reagents and Animals Required:

| Group | Treatment | Dose (ug) | Number of Animals | # of Animals to Challenge | Challenge Dose | Challenge Virus |
|---|---|---|---|---|---|---|
| Grp 1 | PE-87 | 300 | 10 | 10 | 1000 pfu | SUDV |
| Grp 2 | PE-24 | 300 | 10 | 10 | 1000 pfu | SUDV |
| Grp 3 | PE-16 | 300 | 10 | 10 | 1000 pfu | SUDV |
| Grp 4 | PBS | n/a | 10 | 10 | 1000 pfu | SUDV |
| | Total | | 40 | 40 | | |

Species: IFNa/bR KO;
Number of pans: 4;
Days Required: 21;
mAb: 300 ug/dose (20 mg/kg): 300 ul of stock mAb per mouse

| Time Line | | |
|---|---|---|
| Day | Date | Task |
| 0 | 4 Feb. 2016 | Challenge I.P. |
| 1 | 5 Feb. 2016 | Treat I.P. with 300 ul per mouse |
| 4 | 8 Feb. 2016 | Treat I.P. with 300 ul per mouse |
| 21 | 25 Feb. 2016 | Terminate Study |

Materials and Methods 2

Cells

Vero African grivet monkey cells and 293T human embryonic kidney fibroblast cells were maintained in high-glucose Dulbecco's modified Eagle medium (DMEM; Thermo Fisher) supplemented with 10% fetal bovine serum (Atlanta Biologicals), 1% GlutaMAX (Thermo Fisher), and 1% penicillin-streptomycin (Thermo Fisher). Cells were maintained in a humidified 37° C., 5% CO2 incubator.

Vesicular Stomatitis Virus (VSV) Recombinants and Pseudotypes

Recombinant vesicular stomatitis Indiana viruses (rVSV) expressing eGFP in the first position, and encoding representative GP proteins from EBOV/Mayinga (EBOV/H.sap-tc/COD/76/Yambuku-Mayinga), EBOV/Makona (EBOV/H.sap-rec/LBR/14/Makona-L2014), BDBV (BDBV/H.sap/UGA/07/But-811250), SUDV/Boneface (SUDV/C.por-lab/SSD/76/Boneface), RESTV (RESTV/M.fas-tc/USA/89/Phi89-AZ-1435), and LLOV (LLOV/M.sch-wt/ESP/03/Asturias-Bat86), in place of VSV G have been described previously [1-3]. VSV pseudotypes bearing eGFP and GP proteins from TAFV (TAFV/H.sap-tc/CIV/94/CDC807212) and MARV (MARV/H.sap-tc/KEN/80/Mt. Elgon-Musoke) were generated as described [4].

Generation of Cleaved VSV-GP Particles and GPΔTM Ectodomain Proteins

In some experiments, cleaved viral particles bearing $GP_{CL}$ were first generated by incubation with thermolysin (200 µg/mL, pH 7.5, 37° C. for 1 h; Sigma-Aldrich) or recombinant human cathepsin L (CatL, 2 ng/µL, pH 5.5, 37° C. for 1 h; R&D Systems), as described previously [1]. Reactions were stopped by removal onto ice and addition of phosphoramidon (1 mM) or E-64 (10 µM), respectively, and viral particles were used immediately for infectivity assays. A recombinant, soluble GPΔTM protein [5] was also essentially as described above.

VSV Infectivity Measurements and Neutralization Assays

Viral infectivities were measured by automated counting of eGFP+ cells (infectious units; IU) using a CellInsight CX5 imager (Thermo Fisher) at 12-14 h post-infection. For mAb neutralization experiments, pre-titrated amounts of VSV-GP particles (MOI≈IU per cell) were incubated with increasing concentrations of test mAb at room temp for 1 h, and then added to confluent cell monolayers in 96-well plates. Viral neutralization data were subjected to nonlinear regression analysis to derive $EC_{50}$ values (4-parameter, variable slope sigmoidal dose-response equation; GraphPad Prism).

TABLE 6 rVSV-GP neutralization IC50 (nM)[1]

| mAb | EBOV | BDBV | TAFV | SUDV | RESTV |
|---|---|---|---|---|---|
| PE-16 | 0.2 | 0.6 | 4.8 | —[2] | — |
| PE-05 | 9.0 | 4.0 | 0.8 | 34 | 22 |
| PE-24 | 2.0 | 1.0 | 1.5 | 0.5 | 0.2 |
| PE-87 | 0.5 | 0.5 | 1.0 | 0.3 | 0.2 |
| PE-64 | 2.5 | 0.4 | 8 | 40 | — |

[1]$IC_{50}$ (nM), mAb concentration that affords half-maximal neutralization of viral infectivity.
[2]No detectable neutralizing activity.

Authentic Filoviruses and Microneutralization Assays

The authentic filoviruses EBOV/"Zaire 1995" (EBOV/H.sap-tc/COD/95/Kik-9510621) [6], mouse-adapted EBOV/Mayinga (EBOV-MA) [7], SUDV/Boneface-USAMRIID111808, and BDBV/200706291 [8] were used in this study. Antibodies were diluted to indicated concentrations in culture media and incubated with virus for 1 h. Vero E6 cells were exposed to antibody/virus inoculum at an MOI of 0.2 (EBOV, BDBV) or 0.5 (SUDV) plaque-forming unit (PFU)/cell for 1 h. Antibody/virus inoculum was then removed and fresh culture media was added. At 48 h post-infection, cells were fixed, and infected cells were immunostained and quantitated by automated fluorescence microscopy, as described [3].

TABLE 7

Authentic virus neutralization IC50 (nM)[1]

| mAb | EBOV | BDBV | SUDV |
|---|---|---|---|
| PE-16 | 0.1 | 0.3 | 300 |
| PE-05 | 5.2 | —[2] | — |
| PE-24 | 0.7 | 0.6 | 0.2 |
| PE-87 | 0.2 | 0.6 | 0.2 |
| PE-64 | 0.6 | 1.5 | 120 |

[1]$IC_{50}$ (nM), mAb concentration that affords half-maximal neutralization of viral infectivity.
[2]No detectable neutralizing activity.

Generation of mAbs

Recombinant mAbs from the human EBOV disease survivor, as well as germline-reverted (IGL) mAb constructs and WT:IGL chimeras of PE-87 were expressed in Saccha-

*romyces cerevisiae* and purified from cell supernatants by protein A affinity chromatography, as described previously [5]. Other recombinant mAbs were produced in 293F cells by transient transfection, and purified by protein A affinity chromatography, as described previously [3].

ELISAs for GP:mAb Binding

To identify GP cross-reactive mAbs, normalized amounts of rVSVs bearing EBOV, BDBV, and SUDV GP were coated onto plates at 4° C. Plates were then blocked with PBS containing 3% bovine serum albumin (PBSA), and incubated with dilutions of test antibody (5, 50 nM). Bound Abs were detected with anti-human IgG conjugated to horseradish peroxidase (Santa Cruz Biotechnology) and Ultra-TMB colorimetric substrate (Thermo Fisher). All incubations were performed for 1 h at 37° C.

Competition ELISAs for GP/mAb Binding to NPC1

The viral lipid envelopes of rVSV-EBOV GP particles were labeled with biotin using a function-spacer-lipid construct (FSL-biotin) (Sigma-Aldrich) for 1 h at pH 7.5 and 37° C., as described [2]. Biotinylated viral particles bearing $GP_{CL}$ were generated by incubation with thermolysin, and then captured onto high-binding 96-well ELISA plates precoated with recombinant streptavidin (0.65 μg/mL; Sigma-Aldrich). Plates were then blocked with PBSA, and incubated with serial dilutions of test mAbs. Washed plates were then incubated with a pre-titrated concentration of soluble, FLAG epitope-tagged, NPC1 domain C (NPC1-C) protein [9], and bound NPC1-C was detected with an anti-FLAG antibody conjugated to horseradish peroxidase (Sigma-Aldrich). All incubations were performed for 1 h at 37° C.

ELISAs and Immunoblots to Detect mAb Inhibition of GP Cleavage

We used exposure of the NPC1-binding site in EBOV $GP_{CL}$ as a proxy for successful GP4→$GP_{CL}$ cleavage by CatL. rVSV-EBOV GP particles, biotinylated as above, were preincubated with mixtures of test mAb and irrelevant human IgG (test mAb at 50, 250, or 1000 nM; 1000 nM total IgG per reaction) for 1 h at pH 5.5 and 37° C. Reactions were then incubated with CatL (4 ng/μL and 37° C. for 30 min). Reactions were then stopped with E-64, readjusted to neutral pH with PBS, and captured onto streptavidin-coated ELISA plates. NPC1-C binding was measured as above.

Samples treated with the highest concentration of test mAb were also subjected to western blotting. Cleaved GP1 species were detected by immunoblotting with h21D10 mAb (a gift from Dr. Javad Aman) directly conjugated to horseradish peroxidase.

Selection of Viral Neutralization Escape Mutants

Escape mutant selections were performed by serial passage of rVSV-GP particles in the presence of test mAb. Briefly, serial 3-fold dilutions of virus were preincubated with a concentration of mAb corresponding to the $IC_{90}$ value derived from neutralization assays, and then added to confluent monolayers of Vero cells in 12-well plates, in duplicate. Infection was allowed to proceed to completion (>90% cell death by eye), and supernatants were harvested from the infected wells that received the highest dilution (i.e., the least amount) of viral inoculum. Following three subsequent passages under mAb selection with virus-containing supernatants as above, supernatants from passage 4 were tested for viral neutralization escape. If resistance was evident, individual viral clones were plaque-purified on Vero cells, and their GP gene sequences were determined as described previously [1]. The following escape mutant selections were performed: PE-16 with rVSV-EBOV GP/Makona, PE-24 with rVSV-SUDV GP/Boneface, PE-05 with rVSV-EBOV/Mayinga, and PE-64 with rVSV-BDBVΔMuc.

Single-Particle Electron Microscopy

Antibody Fabs and a EBOV GPΔTM ectodomain protein were prepared as described previously [5], and incubated at a ratio of 10:1 (Fab:GP) overnight at 4° C. Complexes were then deposited onto a carbon-coated copper mesh grid, and stained with 1% uranyl formate. Samples were imaged on a Tecnai F12 microscope using the automated image acquisition software Leginon [10]. Images were collected with a Tietz 4K CMOS detector at 52,000× magnification, resulting in a final pixel size of 2.05 A at the specimen level. Images were automatically uploaded to and processed within our Appion database [11]. Individual complexes were extracted from raw images using DoG Picker [12], binned by 2, and placed into a stack. The stack was then subjected to reference-free 2D classification using MRA/MSA [13]. Class averages that did not respond to Fab:EBOV GPΔTM complexes were removed from all subsequent analyses. A subset of 2D class averages was used to create an initial model using common lines within EMAN2 [14]. The raw particle stack was then refined against the initial model using EMAN2 to yield the final 3D volumes. UC SF Chimera was used for modeling and figure generation [15].

GP:mAb Kinetic Binding Binding Analysis by Biolayer Interferometry (BLI)

The OCTETRED™ system (ForteBio, Pall LLC) was used to determine the binding properties of different IgGs to various forms of EBOV GP. Anti-human Fc (AHC) capture sensors (ForteBio) were used for initial mAb loading at 25 mg/mL in 1× kinetics buffer (PBS supplemented with 0.002% Tween-20 and 1 mg/mL of BSA). Binding to GP was performed across two-fold serial dilutions of EBOV GPΔTM or $GP_{CL}$. The baseline and dissociation steps were carried out in the 1× kinetics buffer as per the instrument manufacturer's recommendations. For analysis of binding at pH 5.5, a 1× pH 5.5 kinetics buffer (50 mM sodium citrate dihydrate[pH 5.5], 150 mM sodium chloride, 0.002% Tween-20 and 1 mg/mL BSA) was used in place of the PBS-based 1× kinetic buffer for all steps. For all of the kinetics experiments, a global data fitting to a 1:1 binding model was used to estimate values for the $k_{on}$ (association rate constant), $k_{off}$ (dissociation rate constant), and $K_D$ (equilibrium dissociation constant).

TABLE 8

$K_D$ and $IC_{50}$ values for PE-87 and PE-87 CDR-H3 mutations

| Ligand | Analyte | $K_D$(nM) | EBOV[1] | BDBV[1] | TAFV[1] | SUDV[1] | RESTV[1] |
|---|---|---|---|---|---|---|---|
| PE-87 | GP/$GP_{CL}$ | <0.001 | 1.0 | 0.4 | 0.9 | 0.8 | 0.1 |
| D99A[2] | GP | 74 ± 1 | >500 | nn | >350 | nn | nn |
| H100A[2] | GP | 4.5 ± 0.2 | 1.0 | 0.4 | 0.8 | 1.0 | 0.2 |
| R101A[2] | GP | 9.4 ± 0.3 | 3.2 | 0.4 | 1.9 | 1.5 | 0.2 |
| V102A[2] | GP | 4.0 ± 0.1 | 0.6 | 0.2 | 1.0 | 1.1 | 0.2 |
| W103A[2] | GP | 1.3 ± 0.1 | nn | >200 | >150 | nn | nn |

TABLE 8-continued $K_D$ and $IC_{50}$ values for PE-87 and PE-87 CDR-H3 mutations

| Ligand | Analyte | $K_D$(nM) | EBOV[1] | BDBV[1] | TAFV[1] | SUDV[1] | RESTV[1] |
|---|---|---|---|---|---|---|---|
| G106A[2] | GP | .03 ± .01 | 0.8 | 0.4 | 0.8 | 0.9 | 0.2 |
| Y107A[2] | GP | 30 ± 1 | 3.0 | 0.8 | 0.8 | >350 | 1.3 |
| H108A[2] | GP | 18 ± 0.4 | 3.2 | 0.6 | 2.2 | 2.1 | 0.5 |
| F109A[2] | GP | 37 ± 1 | 4.2 | 0.3 | 2.8 | 2.1 | 0.4 |
| D110A[2] | GP | 1.3 ± 0.3 | 2.0 | 0.9 | 2.1 | 1.5 | 0.4 |
| Y111A[2] | GP | 5.9 ± 0.3 | 0.8 | 0.4 | 1.1 | 0.8 | 0.1 |

[1]$IC_{50}$ (nM), mAb concentration that affords half-maximal neutralization of viral infectivity.
[2]Mutation in CDR3 of PE87.

EBOV and SUDV Challenge Studies in Mice 10-12 week old female BALB/c mice (Jackson Labs) were challenged via the intraperitoneal (i.p.) route with EBOV-MA (100 PFU; ~3,000 $LD_{50}$). Mice were treated i.p. 2 days post-challenge with PBS vehicle or 300 μg of each mAb (0.3 mL volume, ≈15 mg mAb/kg). Animals were observed daily for clinical signs of disease and lethality. Daily observations were increased to a minimum of twice daily while mice were exhibiting signs of disease. Moribund mice were humanely euthanized on the basis of IACUC-approved criteria.

6-8 week old male and female Type 1 IFN α/β receptor knockout mice (Type 1 IFNα/β R-/-) (Jackson Labs) were challenged with WT SUDV (1000 PFU i.p.). Animals were treated i.p. 1 and 4 days post-challenge with PBS vehicle or 300 μg (≈15 mg mAb/kg) per dose, and monitored and euthanized as above.

TABLE 9

Activity in mouse models

| | Mouse efficacy (% survival) | |
|---|---|---|
| mAb | EBOV | SUDV |
| PE-05 | 90 | — |
| PE-87 | 80 | 100 |
| PE-16 | 70 | 20 |
| PE-47 | 90 | 100 |
| PE-24 | 100 | 90-100 |

EBOV mouse studies (n = 10-30) were performed by Dr. J. Dye or P. Glass (USAMRIID) with mAb dosing (5-20 mg/kg) two days post-infection;
SUDV mouse studies (n = 10) were performed by Dr. Dye with 10-20 mg/kg of mAb dosed one and four days post-infection.

BDBV Challenge Studies in Ferrets

Six-month-old female ferrets (*Mustela putorius furo*) were challenged via the intramuscular (i.m.) route with WT BDBV (BDBV/H.sap-tc/UGA/07/Butalya-811250; 1000 $TCID_{50}$ in 0.5 mL volume), as described previously [16]. Animals were treated i.p. 3 and 6 days post-challenge with either PBS vehicle or 15 mg (day 3) and 10 mg (day 6) of each mAb (2 mL volume/dose). Additionally, 1 mL blood was taken from each animal on days 0, 3, 6, 10, 14, 21, 28 days post-infection to determine viral load, measure complete blood counts, and evaluate biochemical markers. Animals were were monitored twice daily for signs of disease during the course of the experiment.

Animal Welfare Statement

Murine challenge studies were conducted under IACUC-approved protocols in compliance with the Animal Welfare Act, PHS Policy, and other applicable federal statutes and regulations relating to animals and experiments involving animals. The dfacility where these studies was conducted (USAMRIID) isaccredited by the Association for Assessment and Accreditation of Laboratory Animal Care, International (AAALAC) and adhere to principles stated in the Guide for the Care and Use of Laboratory Animals, National Research Council, 2011.

Ferret challenge studies were approved by the Animal Care Committee (ACC) of the Canadian Science Centre for Human and Animal Health (CSCHAH) in Winnipeg, Canada, in accordance with guidelines from the Canadian Council on Animal Care (CCAC).

Statistical Analysis

Dose-response neutralization curves were fit to a logistic equation by nonlinear regression analysis. 95% confidence intervals (95% CI) for the extracted $IC_{50}$ parameter were estimated under the assumption of normality. Analysis of survival curves was performed with the Mantel-Cox (log-rank) test. Statistical comparisons of viral titers were carried out with an unpaired t-test. Testing level (alpha) was 0.05 for all statistical tests. All analyses were carried out in GraphPad Prism.

References for Materials and Methods 2

1. Wong, A. C., et al., *A forward genetic strategy reveals destabilizing mutations in the Ebolavirus glycoprotein that alter its protease dependence during cell entry*. J Virol, 2010. 84(1): p. 163-75.
2. Ng, M., et al., *Cell entry by a novel European filovirus requires host endosomal cysteine proteases and Niemann-Pick C1*. Virology, 2014. 468-470: p. 637-46.
3. Wec, A. Z., et al., *A "Trojan horse" bispecific antibody strategy for broad protection against ebolaviruses*. Science, 2016.
4. Takada, A., et al., *A system for functional analysis of Ebola virus glycoprotein*. Proc Natl Acad Sci USA, 1997. 94(26): p. 14764-9.
5. Bornholdt, Z. A., et al., *Isolation of potent neutralizing antibodies from a survivor of the 2014 Ebola virus outbreak*. Science, 2016. 351(6277): p. 1078-83.
6. Jahrling, P. B., et al., *Evaluation of immune globulin and recombinant interferon-alpha2b for treatment of experimental Ebola virus infections*. J Infect Dis, 1999. 179 Suppl 1: p. S224-34.
7. Bray, M., et al., *A mouse model for evaluation of prophylaxis and therapy of Ebola hemorrhagic fever*. J Infect Dis, 1998. 178(3): p. 651-61.
8. Towner, J. S., et al., *Newly discovered ebola virus associated with hemorrhagic fever outbreak in Uganda*. PLoS Pathog, 2008. 4(11): p. e1000212.
9. Bornholdt, Z. A., et al., *Host-Primed Ebola Virus GP Exposes a Hydrophobic NPC1 Receptor Binding Pocket, Revealing a Target for Broadly Neutralizing Antibodies*. MBio, 2015. 7(1).

10. Suloway, C., et al., *Automated molecular microscopy: the new Leginon system*. J Struct Biol, 2005. 151(1): p. 41-60.
11. Lander, G. C., et al., *Appion: an integrated, database-driven pipeline to facilitate EM image processing*. J Struct Biol, 2009. 166(1): p. 95-102.
12. Voss, N. R., et al., *DoG Picker and TiltPicker: software tools to facilitate particle selection in single particle electron microscopy*. J Struct Biol, 2009. 166(2): p. 205-13.
13. Ogura, T., K. Iwasaki, and C. Sato, *Topology representing network enables highly accurate classification of protein images taken by cryo electron-microscope without masking*. J Struct Biol, 2003. 143(3): p. 185-200.
14. Tang, G., et al., *EMAN2: an extensible image processing suite for electron microscopy*. J Struct Biol, 2007. 157(1): p. 38-46.
15. Goddard, T. D., C. C. Huang, and T. E. Ferrin, *Visualizing density maps with UCSF Chimera*. J Struct Biol, 2007. 157(1): p. 281-7.
16. Kozak, R., et al., *Ferrets Infected with Bundibugyo Virus or Ebola Virus Recapitulate Important Aspects of Human Filovirus Disease*. J Virol, 2016. 90(20): p. 9209-23.

References for Background, Summary, Materials and Methods 1

1. Kuhn, J. H., et al., *Nomenclature-and database-compatible names for the two Ebola virus variants that emerged in Guinea and the Democratic Republic of the Congo in 2014*. Viruses, 2014. 6(11): p. 4760-99.
2. Feldmann, H. and M. P. Kiley, *Classification, structure, and replication of filoviruses*. Curr Top Microbiol Immunol, 1999. 235: p. 1-21.
3. Dye, J. M., et al., *Postexposure antibody prophylaxis protects nonhuman primates from filovirus disease*. Proc Natl Acad Sci USA, 2012. 109(13): p. 5034-9.
4. Garbutt, M., et al., *Properties of replication-competent vesicular stomatitis virus vectors expressing glycoproteins of filoviruses and arenaviruses*. J Virol, 2004. 78(10): p. 5458-65.
5. Marzi, A., et al., *Protective efficacy of neutralizing monoclonal antibodies in a nonhuman primate model of Ebola hemorrhagic fever*. PLoS One, 2012. 7(4): p. e36192.
6. Olinger, G. G., Jr., et al., *Delayed treatment of Ebola virus infection with plant-derived monoclonal antibodies provides protection in rhesus macaques*. Proc Natl Acad Sci USA, 2012. 109(44): p. 18030-5.
7. Qiu, X., et al., *Successful treatment of ebola virus-infected cynomolgus macaques with monoclonal antibodies*. Sci Transl Med, 2012. 4(138): p. 138ra81.
8. Pettitt, J., et al., *Therapeutic intervention of Ebola virus infection in rhesus macaques with the MB-003 monoclonal antibody cocktail*. Sci Transl Med, 2013. 5(199): p. 199ra113.
9. Qiu, X., et al., *Reversion of advanced Ebola virus disease in nonhuman primates with ZMapp*. Nature, 2014. 514(7520): p. 47-53.
10. Lee, J. E., et al., *Structure of the Ebola virus glycoprotein bound to an antibody from a human survivor*. Nature, 2008. 454(7201): p. 177-82.
11. Nanbo, A., et al., *Ebolavirus is internalized into host cells via macropinocytosis in a viral glycoprotein-dependent manner*. PLoS Pathog, 2010. 6(9): p. e1001121.
12. Saeed, M. F., et al., *Cellular entry of ebola virus involves uptake by a macropinocytosis-like mechanism and subsequent trafficking through early and late endosomes*. PLoS Pathog, 2010. 6(9): p. e1001110.
13. Chandran, K., et al., *Endosomal proteolysis of the Ebola virus glycoprotein is necessary for infection*. Science, 2005. 308(5728): p. 1643-5.
14. Dube, D., et al., *The primed ebolavirus glycoprotein (19-kilodalton GP1,2): sequence and residues critical for host cell binding*. J Virol, 2009. 83(7): p. 2883-91.
15. Carette, J. E., et al., *Ebola virus entry requires the cholesterol transporter Niemann-Pick C1*. Nature, 2011. 477(7364): p. 340-3.
16. Cote, M., et al., *Small molecule inhibitors reveal Niemann-Pick C1 is essential for Ebola virus infection*. Nature, 2011. 477(7364): p. 344-8.
17. Cook, J. D. and J. E. Lee, *The secret life of viral entry glycoproteins: moonlighting in immune evasion*. PLoS Pathog, 2013. 9(5): p. e1003258.
18. Saphire, E. O., *An update on the use of antibodies against the filoviruses*. Immunotherapy, 2013. 5(11): p. 1221-33.
19. Maruyama, T., et al., *Ebola virus can be effectively neutralized by antibody produced in natural human infection*. J Virol, 1999. 73(7): p. 6024-30.

20. Dias, J. M., et al., *A shared structural solution for neutralizing ebolaviruses*. Nat Struct Mol Biol, 2011. 18(12): p. 1424-7.

21. Murin, C. D., et al., *Structures of protective antibodies reveal sites of vulnerability on Ebola virus*. Proc Natl Acad Sci USA, 2014. 111(48): p. 17182-7.

22. Volchkov, V. E., et al., *Processing of the Ebola virus glycoprotein by the proprotein convertase furin*. Proc Natl Acad Sci USA, 1998. 95(10): p. 5762-7.

23. Kuhn, J. H., et al., *Conserved receptor-binding domains of Lake Victoria marburgvirus and Zaire ebolavirus bind a common receptor*. J Biol Chem, 2006. 281(23): p. 15951-8.

24. Qiu, X., et al., *Characterization of Zaire ebolavirus glycoprotein-specific monoclonal antibodies*. Clin Immunol, 2011. 141(2): p. 218-27.

25. Qiu, X., et al., *Ebola GP-specific monoclonal antibodies protect mice and guinea pigs from lethal Ebola virus infection*. PLoS Negl Trop Dis, 2012. 6(3): p. e1575.

26. Chen, G., et al., *Synthetic antibodies with a human framework that protect mice from lethal Sudan ebolavirus challenge*. ACS Chem Biol, 2014. 9(10): p. 2263-73.

27. Tiller, T., et al., *Efficient generation of monoclonal antibodies from single human B cells by single cell RT-PCR and expression vector cloning*. J Immunol Methods, 2008. 329(1-2): p. 112-24.

28. Swers, J. S., B. A. Kellogg, and K. D. Wittrup, *Shuffled antibody libraries created by in vivo homologous recombination and yeast surface display*. Nucleic Acids Res, 2004. 32(3): p. e36.

29. Gietz, R. D. and R. H. Schiestl, *High-efficiency yeast transformation using the LiAc/SS carrier DNA/PEG method*. Nat Protoc, 2007. 2(1): p. 31-4.

30. Hashiguchi, T., et al., *Structural basis for Marburg virus neutralization by a cross-reactive human antibody*. Cell, 2015. 160(5): p. 904-12.

31. Bowley, D. R., et al., *Antigen selection from an HIV-1 immune antibody library displayed on yeast yields many novel antibodies compared to selection from the same library displayed on phage.* Protein Eng Des Sel, 2007. 20(2): p. 81-90.
32. Honnold, S. P., et al., *Second generation inactivated eastern equine encephalitis virus vaccine candidates protect mice against a lethal aerosol challenge.* PLoS One, 2014. 9(8): p. e104708.
33. Subway, C., et al., *Automated molecular microscopy: the new Leginon system.* J Struct Biol, 2005. 151(1): p. 41-60.
34. Lander, G. C., et al., *Appion: an integrated, database-driven pipeline to facilitate EM image processing.* J Struct Biol, 2009. 166(1): p. 95-102.
35. Voss, N. R., et al., *DoG Picker and TiltPicker: software tools to facilitate particle selection in single particle electron microscopy.* J Struct Biol, 2009. 166(2): p. 205-13.
36. Tang, G., et al., *EMAN2: an extensible image processing suite for electron microscopy.* J Struct Biol, 2007. 157(1): p. 38-46.
37. Goddard, T. D., C. C. Huang, and T. E. Ferrin, *Visualizing density maps with UCSF Chimera.* J Struct Biol, 2007. 157(1): p. 281-7.
38. Bray, M., et al., *A mouse model for evaluation of prophylaxis and therapy of Ebola hemorrhagic fever.* J Infect Dis, 1999. 179 Suppl 1: p. S248-58.

What is claimed is:

1. A monoclonal antibody or an antigen binding fragment thereof comprising
    a heavy chain CDR1 comprising SEQ ID NO: 41, a heavy chain CDR2 comprising SEQ ID NO: 42, a heavy chain CDR3 comprising an amino acid sequence with zero or one amino acid substitution relative to SEQ ID NO: 43, wherein the one amino acid substitution occurs at amino acid residue 100, 101, 102, 106, 107, 108, 109, 110, or 111 in the heavy chain, using SEQ ID NO: 15 as a reference; and
    a light chain CDR1 comprising SEQ ID NO: 44, a light chain CDR2 comprising SEQ ID NO: 45, and a light chain CDR3 comprising SEQ ID NO: 46;
    wherein the antigen to which the antigen binding fragment binds comprises Ebola glycoprotein, and wherein the one amino acid substitution, if present, is selected from the group consisting of H100A, R101A, V102A, G106A, Y107A, H108A, F109A, D110A, and Y111A.

2. The monoclonal antibody of claim 1, wherein said monoclonal antibody or antigen binding fragment thereof comprises a heavy chain variable region comprising an amino acid sequence at least 90% identical to SEQ ID NO: 15; and a light chain variable region comprising an amino acid sequence at least 90% identical to SEQ ID NO: 18.

3. The monoclonal antibody of claim 1, wherein the monoclonal antibody or antigen binding fragment that binds to an Ebola glycoprotein antigen thereof comprises predominantly a single glycoform.

4. The monoclonal antibody of claim 3, wherein the single glycoform is one of GnGn, G1/G2, and NaNa.

5. The monoclonal antibody of claim 3, wherein the single glycoform substantially lacks at least one of fucose and xylose.

6. A composition for treating Ebola, wherein the composition comprises a therapeutically effective amount of a monoclonal antibody and a pharmaceutically acceptable excipient or carrier,
    wherein the monoclonal antibody or an antigen binding fragment thereof comprises a heavy chain CDR1 comprising SEQ ID NO: 41, a heavy chain CDR2 comprising SEQ ID NO: 42, a heavy chain CDR3 comprising an amino acid sequence with zero or one amino acid substitution relative to SEQ ID NO: 43, wherein the one amino acid substitution occurs at amino acid residue 100, 101, 102, 106, 107, 108, 109, 110, or 111 in the heavy chain, using SEQ ID NO: 15 as a reference,
    a light chain CDR1 comprising SEQ ID NO: 44, a light chain CDR2 comprising SEQ ID NO: 45, and a light chain CDR3 comprising SEQ ID NO: 46;
    wherein the antigen to which the antigen binding fragment binds comprises Ebola glycoprotein, and wherein the one amino acid substitution, if present, is selected from the group consisting of H100A, R101A, V102A, G106A, Y107A, H108A, F109A, D110A, and Y111A.

7. The composition of claim 6, wherein the composition further comprises a second monoclonal antibody or antigen binding fragment thereof, wherein said second monoclonal antibody or antigen binding fragment thereof binds Ebola glycoprotein.

8. The composition of claim 7, wherein the second monoclonal antibody or antigen binding fragment thereof comprises a heavy chain CDR1 comprising SEQ ID NO: 53, a heavy chain CDR2 comprising SEQ ID NO: 54, a heavy chain CDR3 comprising SEQ ID NO: 55, and
    a light chain CDR1 comprising SEQ ID NO: 56, a light chain CDR2 comprising SEQ ID NO: 57, and a light chain CDR3 comprising SEQ ID NO: 58, wherein the antigen to which the antigen binding fragment binds comprises an Ebola glycoprotein.

9. The composition of claim 7, wherein said second antibody or antigen binding fragment thereof comprises a heavy chain variable region comprising an amino acid sequence at least 90% identical to SEQ ID NO: 12; and a light chain variable region comprising an amino acid sequence at least 90% identical to SEQ ID NO: 14.

10. The composition of claim 7 further comprising a third monoclonal antibody or antigen binding fragment thereof, wherein said third monoclonal antibody or antigen binding fragment thereof binds an Ebola glycoprotein.

11. A method for treating Ebola infection in a patient, the method comprising administering to the patient a composition comprising a therapeutically effective amount of a first monoclonal antibody or an antigen binding fragment thereof,
    wherein the monoclonal antibody or an antigen binding fragment thereof comprises a heavy chain CDR1 comprising SEQ ID NO: 41, a heavy chain CDR2 comprising SEQ ID NO: 42, a heavy chain CDR3 comprising an amino acid sequence with zero or one amino acid substitution relative to SEQ ID NO: 43, wherein the one amino acid substitution occurs at amino acid residue 100, 101, 102, 106, 107, 108, 109, 110, or 111 in the heavy chain, using SEQ ID NO: 15 as a reference, and
    a light chain CDR1 comprising SEQ ID NO: 44, a light chain CDR2 comprising SEQ ID NO: 45, and a light chain CDR3 comprising SEQ ID NO: 46;
    wherein the antigen to which the antigen binding fragment binds comprises Ebola glycoprotein, and wherein the one amino acid substitution, if present, is selected from the group consisting of H100A, R101A, V102A, G106A, Y107A, H108A, F109A, D110A, and Y111A.

12. The method of claim 11, wherein said monoclonal antibody or antigen binding fragment thereof comprises a heavy chain variable region comprising an amino acid sequence at least 90% identical to SEQ ID NO: 15; and a light chain variable region comprising an amino acid sequence at least 90% identical to SEQ ID NO: 18.

13. The method of claim 11, wherein the composition further comprises a second antibody, wherein the second antibody or antigen binding fragment thereof comprises a heavy chain CDR1 comprising SEQ ID NO: 53, a heavy chain CDR2 comprising SEQ ID NO: 54, a heavy chain CDR3 comprising SEQ ID NO: 55, and a light chain CDR1 comprising SEQ ID NO: 56, a light chain CDR2 comprising SEQ ID NO: 57, and a light chain CDR3 comprising SEQ ID NO: 58, wherein the antigen to which the antigen binding fragment binds comprises an Ebola glycoprotein.

14. The method of claim 13, wherein said second antibody or antigen binding fragment thereof comprises a heavy chain variable region comprising an amino acid sequence at least 90% identical to SEQ ID NO: 12; and a light chain variable region comprising an amino acid sequence at least 90% identical to SEQ ID NO: 14.

15. The method of claim 13, wherein said first and said second monoclonal antibodies or antigen binding fragments thereof each bind at least two species of Ebola glycoprotein.

16. The method of claim 13, wherein the first and the second monoclonal antibodies or antigen binding fragments thereof that bind to an Ebola glycoprotein antigen comprise predominantly single glycoforms.

17. The method of claim 13, wherein the predominantly single glycoforms are one of GnGn, G1/G2, and NaNa.

18. The method of claim 13, wherein the predominantly single glycoforms substantially lack at least one of fucose and xylose.

* * * * *

```
                               SEQUENCE LISTING

Sequence total quantity: 76
SEQ ID NO: 1            moltype = AA  length = 15
FEATURE                 Location/Qualifiers
source                  1..15
                        mol_type = protein
                        organism = Homo sapiens
SEQUENCE: 1
AKDHRVWAAG YHFDY                                                            15

SEQ ID NO: 2            moltype = AA  length = 8
FEATURE                 Location/Qualifiers
source                  1..8
                        mol_type = protein
                        organism = Homo sapiens
SEQUENCE: 2
QQYYSSPT                                                                     8

SEQ ID NO: 3            moltype = AA  length = 15
FEATURE                 Location/Qualifiers
source                  1..15
                        mol_type = protein
                        organism = Homo sapiens
SEQUENCE: 3
AKDHRVWAPG YYFDH                                                            15

SEQ ID NO: 4            moltype = AA  length = 8
FEATURE                 Location/Qualifiers
source                  1..8
                        mol_type = protein
                        organism = Homo sapiens
SEQUENCE: 4
QQYNRSPT                                                                     8

SEQ ID NO: 5            moltype = AA  length = 22
FEATURE                 Location/Qualifiers
source                  1..22
                        mol_type = protein
                        organism = Homo sapiens
SEQUENCE: 5
TTYTEDMQYF DWLLRGGETF DY                                                    22

SEQ ID NO: 6            moltype = AA  length = 11
FEATURE                 Location/Qualifiers
source                  1..11
                        mol_type = protein
                        organism = Homo sapiens
SEQUENCE: 6
QQSYSTPGRY T                                                                11

SEQ ID NO: 7            moltype = AA  length = 17
FEATURE                 Location/Qualifiers
source                  1..17
                        mol_type = protein
                        organism = Homo sapiens
SEQUENCE: 7
ARDRYPVLFA TDYGMDV                                                          17

SEQ ID NO: 8            moltype = AA  length = 11
FEATURE                 Location/Qualifiers
source                  1..11
```

```
                        mol_type = protein
                        organism = Homo sapiens
SEQUENCE: 8
QQRSIWPPGV T                                                          11

SEQ ID NO: 9            moltype = AA   length = 19
FEATURE                 Location/Qualifiers
source                  1..19
                        mol_type = protein
                        organism = Homo sapiens
SEQUENCE: 9
TRDGFRGSSW GYSYYGMDV                                                  19

SEQ ID NO: 10           moltype = AA   length = 11
FEATURE                 Location/Qualifiers
source                  1..11
                        mol_type = protein
                        organism = Homo sapiens
SEQUENCE: 10
AAWDDSLNGP V                                                          11

SEQ ID NO: 11           moltype = AA   length = 131
FEATURE                 Location/Qualifiers
source                  1..131
                        mol_type = protein
                        organism = Homo sapiens
SEQUENCE: 11
EVQLVESGGG LVKPGGSLRL SCAASGFTFS NAWMSWVRQA PGKGLEWVGR IKSKTDGGTI     60
DYAAPVKGRF TISRDDSKNT VYLQMTSLKT EDTAVYYCTT YTEDMRYFDW LLRGGETFDY     120
WGQGTLVTVS S                                                          131

SEQ ID NO: 12           moltype = AA   length = 131
FEATURE                 Location/Qualifiers
source                  1..131
                        mol_type = protein
                        organism = Homo sapiens
SEQUENCE: 12
EVQLVESGGG LVKPGGSLRL SCAASGFTFS NAWMSWVRQA PGEGLEWVGR IKSKTDGGTI     60
DYAAPVKGRF TISRDDSKNT VYLQMTSLKT EDTAVYYCTT YTEDMQYFDW LLRGGETFDY     120
WGQGTLVTVS S                                                          131

SEQ ID NO: 13           moltype = AA   length = 109
FEATURE                 Location/Qualifiers
source                  1..109
                        mol_type = protein
                        organism = Homo sapiens
SEQUENCE: 13
DIRLTQSPSS LSASVGDRVT ITCRASHYIS TYLNWYQQKP GKAPKLLIYA ASNLQSGVPS     60
RFSGSGFGTD FSLTISSLQP EDFATYHCQQ SYSTPGRYTF GQGTKVEIK                 109

SEQ ID NO: 14           moltype = AA   length = 109
FEATURE                 Location/Qualifiers
source                  1..109
                        mol_type = protein
                        organism = Homo sapiens
SEQUENCE: 14
DIQMTQSPSS LSASVGDRVT ITCRASQYIS TYLNWYQQKP GKAPKLLIYA AYNLQSGVPS     60
RFSGSGSGTD FTLTISSLQP EDFATYYCQQ SYSTPGRYTF GQGTKVEIK                 109

SEQ ID NO: 15           moltype = AA   length = 122
FEATURE                 Location/Qualifiers
source                  1..122
                        mol_type = protein
                        organism = Homo sapiens
SEQUENCE: 15
QVQLVQSGVT LVQPGGSLRV SCAASGFTFS SYAMSWVRQA PGKGLEWVSA ISGLGGSTYY     60
ADSVKGRFTI SRDNSKNTLY LQMNSLRAED TAVYYCAKDH RVWAAGYHFD YWGQGALVTV     120
SS                                                                    122

SEQ ID NO: 16           moltype = DNA   length = 366
FEATURE                 Location/Qualifiers
source                  1..366
                        mol_type = genomic DNA
                        organism = Homo sapiens
SEQUENCE: 16
caggtccagc tggtgcagtc tggggtaacc ttggtacagc ctgggggtc cctgagagtc      60
tcctgtgcag cctctggatt cacctttagc agctatgcca tgagctgggt ccgccaggct    120
ccagggaagg ggctggagtg gtctcagct attagtggtc ttgcggaag cacatactac      180
gcagactccg tgaagggccg gttcaccatc tccagagaca attccaagaa cacgctgtat    240
```

```
ctgcaaatga acagcctgag agccgaggac acggccgtat attactgtgc gaaagatcat    300
cgggtttggg cagctggata ccactttgac tactggggcc agggagccct ggtcaccgtc    360
tcctca                                                               366

SEQ ID NO: 17           moltype = AA   length = 122
FEATURE                 Location/Qualifiers
source                  1..122
                        mol_type = protein
                        organism = Homo sapiens
SEQUENCE: 17
EVQLVESGGG LVQPGGSLRV SCAASGFTFS SYAMSWVRQA PGKGLEWVSA ISGLGGSTYY    60
ADSVKGRFTI SRDNSKNTLY LQMNSLRAED TAVYYCAKDH RVWAAGYHFD YWGQGTLVTV    120
SS                                                                  122

SEQ ID NO: 18           moltype = AA   length = 106
FEATURE                 Location/Qualifiers
source                  1..106
                        mol_type = protein
                        organism = Homo sapiens
SEQUENCE: 18
DIVLTQSPST LSASVGDRVT ITCRASQSIS SWLAWYQQKP GEAPKLLISD ASSLESGVPS    60
RFSGSGSGTE FTLTISSLQP DDFATYYCQQ YYSSPTFGGG TKVEIK                   106

SEQ ID NO: 19           moltype = DNA   length = 318
FEATURE                 Location/Qualifiers
source                  1..318
                        mol_type = genomic DNA
                        organism = Homo sapiens
SEQUENCE: 19
gatattgtgc tgacccagtc tccttccacc ctgtctgcat ctgtaggaga cagagtcacc    60
atcacttgcc gggccagtca gagtattagt agctggttgg cctggtatca gcagaaacca    120
ggggaagccc ctaaactcct gatctctgat gcctccagtt tggaaagtgg ggtcccatca    180
aggttcagcg gcagtggatc tgggacagaa ttcactctca ccatcagcag cctgcagcct    240
gatgattttg caacttatta ctgccaacag tattatagtt ccccccactt tcggcgaggg    300
accaaggtgg aaatcaaa                                                  318

SEQ ID NO: 20           moltype = AA   length = 106
FEATURE                 Location/Qualifiers
source                  1..106
                        mol_type = protein
                        organism = Homo sapiens
SEQUENCE: 20
DIQMTQSPST LSASVGDRVT ITCRASQSIS SWLAWYQQKP GEAPKLLISD ASSLESGVPS    60
RFSGSGSGTE FTLTISSLQP DDFATYYCQQ YYSSPTFGGG TKVEIK                   106

SEQ ID NO: 21           moltype = AA   length = 122
FEATURE                 Location/Qualifiers
source                  1..122
                        mol_type = protein
                        organism = Homo sapiens
SEQUENCE: 21
EVQLVESGGG LVQPGGSLRL SCAASGFTFS SYAMSWVRQA PGKGLEWVSE ISGLGGSTYY    60
ADSAKGRFTI SRDNSKSTLY LQMNSLRAED TAVYYCAKDH RVWAPGYYFD HWGQGTLVTV    120
SS                                                                  122

SEQ ID NO: 22           moltype = DNA   length = 366
FEATURE                 Location/Qualifiers
source                  1..366
                        mol_type = genomic DNA
                        organism = Homo sapiens
SEQUENCE: 22
gaggtgcagc tggtggagtc gggggggaggc ttggtacagc cggggggggtc cctgagactc   60
tcctgtgcag cctctggatt cacctttagc agctatgcca tgagctgggt ccgccaggct    120
ccaggggaagg ggctggagtg ggtctcggaa attagcggta ttggtggtag cacatactac   180
gcagactccg cgaagggccg gttcaccatc tccagagaca attccaagag cacccctgtat  240
ctgcaaatga acagcctgag agccgaagac acggccgtat attactgtgc gaaagatcat    300
cgcgtttggg cacctggata ttactttgac cactggggcc agggaaccct ggtcactgtc    360
tcctca                                                               366

SEQ ID NO: 23           moltype = AA   length = 106
FEATURE                 Location/Qualifiers
source                  1..106
                        mol_type = protein
                        organism = Homo sapiens
SEQUENCE: 23
DIVLTQSPST LSASVGDRVT ITCRASQSIS SWLAWYQQKP GKAPKLLIYD ASSLESGVPS    60
RFSGSGSGTE FTLTISSLQP DDFATYFCQQ YNRSPTFGGG TKVEIK                   106

SEQ ID NO: 24           moltype = DNA   length = 318
```

| FEATURE | Location/Qualifiers |
|---|---|
| source | 1..318<br>mol_type = genomic DNA<br>organism = Homo sapiens |

SEQUENCE: 24
```
gatattgtgc tgacgcagtc tccttccacc ctgtctgcat ctgtaggaga cagagtcacc   60
atcacttgcc gggccagtca gagtattagt agctggttgg cctggtatca gcagaaacca  120
gggaaagccc ctaaactcct gatctatgat gcctccagtt tggaaagtgg ggtcccatca  180
aggttcagcg gcagtggatc tgggacagaa ttcactctca ccatcagcag cctgcagcct  240
gatgattttg caacttattt ctgccaacag tataataggt cccccacttt cggcggaggg  300
accaaggtgg aaatcaaa                                                318
```

| SEQ ID NO: 25 | moltype = AA   length = 131 |
|---|---|
| FEATURE | Location/Qualifiers |
| source | 1..131<br>mol_type = protein<br>organism = Homo sapiens |

SEQUENCE: 25
```
EVQLVESGGG LVKPGGSLRL SCAASGFTFS NAWMSWVRQA PGEGLEWVGR IKSKTDGGTI   60
DYAAPVKGRF TISRDDSKNT VYLQMTSLKT EDTAVYYCTT YTEDMQYFDW LLRGGETFDY  120
WGQGTLVTVS S                                                       131
```

| SEQ ID NO: 26 | moltype = DNA   length = 393 |
|---|---|
| FEATURE | Location/Qualifiers |
| source | 1..393<br>mol_type = genomic DNA<br>organism = Homo sapiens |

SEQUENCE: 26
```
gaggttcagc ttgttgaatc tggtggtggt cttgtgaagc ctggtggttc tcttagactt   60
agctgtgctg ctagcggttt caccttctct aacgcttgga tgtcttggga tagacagct  120
cctggtgaag gtcttgaatg ggtgggaagg atcaagagca agaccgatgg tggtactatc  180
gattacgctg ctcctgttaa gggaaggttc accatcagca gggatgatag caagaacacc  240
gtgtacctgc agatgacctc tcttaagact gaggataccg ctgtgtacta ctgcactacc  300
tacaccgagg atatgcagta cttcgattgg cttcttaggg gtggtgagac tttcgattat  360
tggggtcagg gtactctggt gaccgtgtca tct                               393
```

| SEQ ID NO: 27 | moltype = AA   length = 109 |
|---|---|
| FEATURE | Location/Qualifiers |
| source | 1..109<br>mol_type = protein<br>organism = Homo sapiens |

SEQUENCE: 27
```
DIQMTQSPSS LSASVGDRVT ITCRASQYIS TYLNWYQQKP GKAPKLLIYA AYNLQSGVPS   60
RFSGSGSGTD FTLTISSLQP EDFATYYCQQ SYSTPGRYTF GQGTKVEIK              109
```

| SEQ ID NO: 28 | moltype = DNA   length = 327 |
|---|---|
| FEATURE | Location/Qualifiers |
| source | 1..327<br>mol_type = genomic DNA<br>organism = Homo sapiens |

SEQUENCE: 28
```
gatattcaga tgacccagtc acctagcagc ctgtctgctt ctgttggtga tagggtgacc   60
attacctgca gggcttctca gtacatcagc acctacctga attggtacca gcagaagcct  120
ggtaaggctc ctaagcttct tatctacgct gcttacaacc tgcagagcgg tgttccttct  180
aggttctctg gttctggaag cggaaccgat ttcccctga ccatttcttc actgcagcct  240
gaggatttcg ctacctatta ctgccagcag agctactcta ctcctggtag gtacactttc  300
ggtcagggta ctaaggttga gatcaag                                      327
```

| SEQ ID NO: 29 | moltype = AA   length = 124 |
|---|---|
| FEATURE | Location/Qualifiers |
| source | 1..124<br>mol_type = protein<br>organism = Homo sapiens |

SEQUENCE: 29
```
QVQLVQSGAE VTKPGASVKV SCKASGYTFT TYYMHWVRQA PGQGLEWVGI INPSGGITRY   60
AQKFQGRVTL TRDTSTTTVY MELSSLRSED TAVYYCARDR YPVLFATDYG MDVWGQGTTV  120
TVSS                                                               124
```

| SEQ ID NO: 30 | moltype = DNA   length = 372 |
|---|---|
| FEATURE | Location/Qualifiers |
| source | 1..372<br>mol_type = genomic DNA<br>organism = Homo sapiens |

SEQUENCE: 30
```
caggtccagc ttgtacagtc tggggctgag gtgacgaagc ctggggcctc agtgaaggtt   60
tcctgcaagg catctggata caccttcacc acctactata tgcactgggt gcgccaggcc  120
cctggacaag gcttgagtg ggtgggaata atcaaccta tggtggtat cacacggtac  180
gcacagaagt tccagggcag agtcaccttg accagggaca cgtccacgac cacagtctac  240
atggagctga gcagcctgag atctgaggac acggccgtgt attactgtgc gagagatcga  300
```

```
taccccgtcc ttttttgcgac cgactacggt atggacgtct ggggccaagg gaccacggtc    360
accgtctcct ca                                                         372
```

SEQ ID NO: 31          moltype = AA   length = 109
FEATURE                Location/Qualifiers
source                 1..109
                       mol_type = protein
                       organism = Homo sapiens
SEQUENCE: 31
```
DIVMTQSPAT LSLSPGERAT LSCRASQSVS GYLAWYQQKP GQAPRLLIYD ASNRATGIPA    60
RFSGSGSGTD FTLTISSLEP EDFAVYYCQQ RSIWPPGVTF GGGTKVEIK               109
```

SEQ ID NO: 32          moltype = DNA   length = 326
FEATURE                Location/Qualifiers
source                 1..326
                       mol_type = genomic DNA
                       organism = Homo sapiens
SEQUENCE: 32
```
gatattgtga tgacacagtc tccagccacc ctgtctttgt ctccagggga aagagccacc    60
ctctcctgca gggccagtca gagtgttagc ggctacttag cctggtacca acagaaacct   120
ggccaggctc ccagactcct catctatgat gcatccaaca gggccactgg catcccagcc   180
aggttcagcg gcagtgggtc tgggacagac ttcactctca ccatcagcag cctagagcct   240
gaagattttg cagtttattac tgtcagcagc gaagcatctg gcctccgggg gtcactttcg   300
gcggagggac caaggtggaa atcaaa                                         326
```

SEQ ID NO: 33          moltype = AA   length = 128
FEATURE                Location/Qualifiers
source                 1..128
                       mol_type = protein
                       organism = Homo sapiens
SEQUENCE: 33
```
QVQLQESGGG LVKPGRSLRL SCTASGFTFG DYAMSWFRQA PGKGLEWVGF LRSKAYGGTA    60
EYAASVKGRF TMSRDDSKSI AYLQMNSLKT EDTAVYFCTR DGFRGSSWGY SYYGMDVWGQ   120
GTTVTVSS                                                             128
```

SEQ ID NO: 34          moltype = DNA   length = 384
FEATURE                Location/Qualifiers
source                 1..384
                       mol_type = genomic DNA
                       organism = Homo sapiens
SEQUENCE: 34
```
caggtgcagc tgcaggagtc ggggggaggc ttggtaaagc cagggcggtc cctgagactc    60
tcctgtacag cttctggatt cacctttggt gattatgcta tgagctggtt ccgccaggct   120
ccagggaagg ggctggagtg ggtaggtttc cttagaagca aagcttatgg tgggacagca   180
gaatacgccg cgtctgtgaa aggcagattc accatgtcaa gagatgattc aaaagcatc    240
gcctatctgc aaatgaacag cctgaaaacc gaggacacag ccgtgtattt ctgtactaga   300
gatggatttc ggggcagcag ctgggggtac tcctactacg gtatggacgt ctggggccaa   360
gggaccacgg tcaccgtctc ctca                                           384
```

SEQ ID NO: 35          moltype = AA   length = 110
FEATURE                Location/Qualifiers
source                 1..110
                       mol_type = protein
                       organism = Homo sapiens
SEQUENCE: 35
```
SYELTQPPSA SGTPGQRVTI SCSGSSSNIG GNTVSWYQQL PGTAPKLLIY TNDQRPSGVP    60
DRFSGSKSGT SASLAISGLQ SEDEADYYCA AWDDSLNGPV FGGGTKLTVL              110
```

SEQ ID NO: 36          moltype = DNA   length = 330
FEATURE                Location/Qualifiers
source                 1..330
                       mol_type = genomic DNA
                       organism = Homo sapiens
SEQUENCE: 36
```
tcctatgagc tgactcagcc accctcagcg tctgggaccc ccgggcagag ggtcaccatc    60
tcttgttctg gaagcagctc caatatcgga ggtaatactg taagctggta ccagcagctc   120
ccaggaacgg ccccccaaact cctcatctat actaatgatc agcggccctc aggggtccct   180
gaccgattct ctggctccaa gtctggcacc tcagcctccc tggccatcag tgggctccag   240
tctgaggatg aggctgatta ttattgtgca gcatgggatg acagcctgaa tggtccggtg   300
ttcggcggag ggaccaagct caccgtccta                                     330
```

SEQ ID NO: 37          moltype = AA   length = 131
FEATURE                Location/Qualifiers
source                 1..131
                       mol_type = protein
                       organism = Homo sapiens
SEQUENCE: 37
```
EVQLVESGGG LVKPGGSLRL SCAASGFTFS NAWMSWVRQA PGKGLEWVGR IKSKTDGGTI    60
DYAAPVKGRF TISRDDSKNT VYLQMTSLKT EDTAVYYCTT YTEDMRYFDW LLRGGETFDY   120
```

WGQGTLVTVS S                                                                 131

SEQ ID NO: 38            moltype = DNA   length = 393
FEATURE                  Location/Qualifiers
source                   1..393
                         mol_type = genomic DNA
                         organism = Homo sapiens
SEQUENCE: 38
gaggtgcagc tggtggagtc tgggggaggc ttggtaaagc ctggggggtc ccttagactc    60
tcctgtgcag cctctggatt cactttcagt aacgcctgga tgagctgggt ccgccaggct   120
ccagggaagg ggctggagtg ggttggccgg attaaaagca aaactgatgg tgggacaata   180
gactacgctg acccgtgaa aggcagattc accatctcaa gagatgattc aaaaaacacg   240
gtgtatctgc aaatgaccag cctgaaaacc gaggacacag ccgtgtatta ctgtaccaca   300
tacacggaag atatgcgata ttttgactgg ttattgcggg gtggggaaac ctttgactac   360
tggggccagg gaaccctggt caccgtctcc tca                                393

SEQ ID NO: 39            moltype = AA   length = 109
FEATURE                  Location/Qualifiers
source                   1..109
                         mol_type = protein
                         organism = Homo sapiens
SEQUENCE: 39
DIRLTQSPSS LSASVGDRVT ITCRASHYIS TYLNWYQQKP GKAPKLLIYA ASNLQSGVPS    60
RFSGSGFGTD FSLTISSLQP EDFATYHCQQ SYSTPGRYTF GQGTKVEIK               109

SEQ ID NO: 40            moltype = DNA   length = 327
FEATURE                  Location/Qualifiers
source                   1..327
                         mol_type = genomic DNA
                         organism = Homo sapiens
SEQUENCE: 40
gacatccggt tgacccagtc tccatcctcc ctgtctgcat ctgtaggaga cagagtcacc    60
atcacttgcc gggcaagtca ctacattagc acctatttaa attggtatca gcagaaacca   120
gggaaagccc ctaagctcct gatctatgct gcatccaatt tacaaagtgg ggtcccatca   180
aggttcagtg gcagtggatt tgggacagat ttctctctca ccatcagcag tctgcaacct   240
gaagatttcg caacttacca ctgtcaacag agttacagta ccccagggag gtacactttt   300
ggccagggga ccaaggtgga aatcaaa                                       327

SEQ ID NO: 41            moltype = AA   length = 10
FEATURE                  Location/Qualifiers
source                   1..10
                         mol_type = protein
                         organism = Homo sapiens
SEQUENCE: 41
GFTFSSYAMS                                                            10

SEQ ID NO: 42            moltype = AA   length = 15
FEATURE                  Location/Qualifiers
source                   1..15
                         mol_type = protein
                         organism = Homo sapiens
SEQUENCE: 42
AISGLGGSTY YADSV                                                      15

SEQ ID NO: 43            moltype = AA   length = 13
FEATURE                  Location/Qualifiers
source                   1..13
                         mol_type = protein
                         organism = Homo sapiens
SEQUENCE: 43
DHRVWAAGYH FDY                                                        13

SEQ ID NO: 44            moltype = AA   length = 11
FEATURE                  Location/Qualifiers
source                   1..11
                         mol_type = protein
                         organism = Homo sapiens
SEQUENCE: 44
RASQSISSWL A                                                          11

SEQ ID NO: 45            moltype = AA   length = 7
FEATURE                  Location/Qualifiers
source                   1..7
                         mol_type = protein
                         organism = Homo sapiens
SEQUENCE: 45
DASSLES                                                                7

SEQ ID NO: 46            moltype = AA   length = 8

```
FEATURE                Location/Qualifiers
source                 1..8
                       mol_type = protein
                       organism = Homo sapiens
SEQUENCE: 46
QQYYSSPT                                                                    8

SEQ ID NO: 47          moltype = AA  length = 10
FEATURE                Location/Qualifiers
source                 1..10
                       mol_type = protein
                       organism = Homo sapiens
SEQUENCE: 47
GFTFSSYAMS                                                                 10

SEQ ID NO: 48          moltype = AA  length = 16
FEATURE                Location/Qualifiers
source                 1..16
                       mol_type = protein
                       organism = Homo sapiens
SEQUENCE: 48
EISGLGGSTY YADSAK                                                          16

SEQ ID NO: 49          moltype = AA  length = 13
FEATURE                Location/Qualifiers
source                 1..13
                       mol_type = protein
                       organism = Homo sapiens
SEQUENCE: 49
DHRVWAPGYY FDH                                                             13

SEQ ID NO: 50          moltype = AA  length = 11
FEATURE                Location/Qualifiers
source                 1..11
                       mol_type = protein
                       organism = Homo sapiens
SEQUENCE: 50
RASQSISSWL A                                                               11

SEQ ID NO: 51          moltype = AA  length = 7
FEATURE                Location/Qualifiers
source                 1..7
                       mol_type = protein
                       organism = Homo sapiens
SEQUENCE: 51
DASSLES                                                                     7

SEQ ID NO: 52          moltype = AA  length = 8
FEATURE                Location/Qualifiers
source                 1..8
                       mol_type = protein
                       organism = Homo sapiens
SEQUENCE: 52
QQYNRSPT                                                                    8

SEQ ID NO: 53          moltype = AA  length = 10
FEATURE                Location/Qualifiers
source                 1..10
                       mol_type = protein
                       organism = Homo sapiens
SEQUENCE: 53
GFTFSNAWMS                                                                 10

SEQ ID NO: 54          moltype = AA  length = 18
FEATURE                Location/Qualifiers
source                 1..18
                       mol_type = protein
                       organism = Homo sapiens
SEQUENCE: 54
RIKSKTDGGT IDYAAPVK                                                        18

SEQ ID NO: 55          moltype = AA  length = 20
FEATURE                Location/Qualifiers
source                 1..20
                       mol_type = protein
                       organism = Homo sapiens
SEQUENCE: 55
YTEDMQYFDW LLRGGETFDY                                                      20
```

```
SEQ ID NO: 56            moltype = AA   length = 11
FEATURE                  Location/Qualifiers
source                   1..11
                         mol_type = protein
                         organism = Homo sapiens
SEQUENCE: 56
RASQYISTYL N                                                          11

SEQ ID NO: 57            moltype = AA   length = 7
FEATURE                  Location/Qualifiers
source                   1..7
                         mol_type = protein
                         organism = Homo sapiens
SEQUENCE: 57
AAYNLQS                                                                7

SEQ ID NO: 58            moltype = AA   length = 11
FEATURE                  Location/Qualifiers
source                   1..11
                         mol_type = protein
                         organism = Homo sapiens
SEQUENCE: 58
QQSYSTPGRY T                                                          11

SEQ ID NO: 59            moltype = AA   length = 10
FEATURE                  Location/Qualifiers
source                   1..10
                         mol_type = protein
                         organism = Homo sapiens
SEQUENCE: 59
GYTFTTYYMH                                                            10

SEQ ID NO: 60            moltype = AA   length = 16
FEATURE                  Location/Qualifiers
source                   1..16
                         mol_type = protein
                         organism = Homo sapiens
SEQUENCE: 60
IINPSGGITR YAQKFQ                                                     16

SEQ ID NO: 61            moltype = AA   length = 15
FEATURE                  Location/Qualifiers
source                   1..15
                         mol_type = protein
                         organism = Homo sapiens
SEQUENCE: 61
DRYPVLFATD YGMDV                                                      15

SEQ ID NO: 62            moltype = AA   length = 11
FEATURE                  Location/Qualifiers
source                   1..11
                         mol_type = protein
                         organism = Homo sapiens
SEQUENCE: 62
RASQSVSGYL A                                                          11

SEQ ID NO: 63            moltype = AA   length = 7
FEATURE                  Location/Qualifiers
source                   1..7
                         mol_type = protein
                         organism = Homo sapiens
SEQUENCE: 63
DASNRAT                                                                7

SEQ ID NO: 64            moltype = AA   length = 11
FEATURE                  Location/Qualifiers
source                   1..11
                         mol_type = protein
                         organism = Homo sapiens
SEQUENCE: 64
QQRSIWPPGV T                                                          11

SEQ ID NO: 65            moltype = AA   length = 10
FEATURE                  Location/Qualifiers
source                   1..10
                         mol_type = protein
                         organism = Homo sapiens
SEQUENCE: 65
GFTFGDYAMS                                                            10
```

-continued

```
SEQ ID NO: 66          moltype = AA   length = 18
FEATURE                Location/Qualifiers
source                 1..18
                       mol_type = protein
                       organism = Homo sapiens
SEQUENCE: 66
FLRSKAYGGT AEYAASVK                                                   18

SEQ ID NO: 67          moltype = AA   length = 17
FEATURE                Location/Qualifiers
source                 1..17
                       mol_type = protein
                       organism = Homo sapiens
SEQUENCE: 67
DGFRGSSWGY SYYGMDV                                                    17

SEQ ID NO: 68          moltype = AA   length = 13
FEATURE                Location/Qualifiers
source                 1..13
                       mol_type = protein
                       organism = Homo sapiens
SEQUENCE: 68
SGSSSNIGGN TVS                                                        13

SEQ ID NO: 69          moltype = AA   length = 7
FEATURE                Location/Qualifiers
source                 1..7
                       mol_type = protein
                       organism = Homo sapiens
SEQUENCE: 69
TNDQRPS                                                                7

SEQ ID NO: 70          moltype = AA   length = 14
FEATURE                Location/Qualifiers
source                 1..14
                       mol_type = protein
                       organism = Homo sapiens
SEQUENCE: 70
WDDSLNGPVF GGGT                                                       14

SEQ ID NO: 71          moltype = AA   length = 10
FEATURE                Location/Qualifiers
source                 1..10
                       mol_type = protein
                       organism = Homo sapiens
SEQUENCE: 71
GFTFSNAWMS                                                            10

SEQ ID NO: 72          moltype = AA   length = 18
FEATURE                Location/Qualifiers
source                 1..18
                       mol_type = protein
                       organism = Homo sapiens
SEQUENCE: 72
RIKSKTDGGT IDYAAPVK                                                   18

SEQ ID NO: 73          moltype = AA   length = 20
FEATURE                Location/Qualifiers
source                 1..20
                       mol_type = protein
                       organism = Homo sapiens
SEQUENCE: 73
YTEDMRYFDW LLRGGETFDY                                                 20

SEQ ID NO: 74          moltype = AA   length = 11
FEATURE                Location/Qualifiers
source                 1..11
                       mol_type = protein
                       organism = Homo sapiens
SEQUENCE: 74
RASHYISTYL N                                                          11

SEQ ID NO: 75          moltype = AA   length = 7
FEATURE                Location/Qualifiers
source                 1..7
                       mol_type = protein
                       organism = Homo sapiens
SEQUENCE: 75
```

```
AASNLQS                                                                         7

SEQ ID NO: 76          moltype = AA   length = 11
FEATURE                Location/Qualifiers
source                 1..11
                       mol_type = protein
                       organism = Homo sapiens
SEQUENCE: 76
QQSYSTPGRY T                                                                   11
```